(12) United States Patent
Bruhlmann et al.

(10) Patent No.: US 8,951,771 B2
(45) Date of Patent: *Feb. 10, 2015

(54) MODIFIED 13-HYDROPEROXIDE LYASES AND USES THEREOF

(71) Applicant: Firmenich SA, Geneva (CH)

(72) Inventors: Fredi Bruhlmann, Geneva (CH); Laurent Fourage, Calvisson (FR); Denis Wahler, Caissargues (FR)

(73) Assignee: Firmenich SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/952,423

(22) Filed: Jul. 26, 2013

(65) Prior Publication Data

US 2014/0024092 A1 Jan. 23, 2014

Related U.S. Application Data

(63) Continuation of application No. 12/664,565, filed as application No. PCT/IB2008/052539 on Jun. 25, 2008, now Pat. No. 8,501,452.

(30) Foreign Application Priority Data

Jun. 28, 2007 (EP) .................................... 07111337

(51) Int. Cl.
*C12N 9/88* (2006.01)
*C12P 7/24* (2006.01)
*C12P 7/04* (2006.01)

(52) U.S. Cl.
CPC ... *C12P 7/04* (2013.01); *C12N 9/88* (2013.01); *C12P 7/24* (2013.01)
USPC ... 435/232; 435/147; 435/252.3; 435/254.11; 435/320.1; 536/23.2

(58) Field of Classification Search
CPC ........... C12N 15/8261; C12N 15/8243; C12N 15/8247; C12N 9/88; C12N 9/96; C12N 9/0077
See application file for complete search history.

(56) References Cited

U.S. PATENT DOCUMENTS

| | | | |
|---|---|---|---|
| 6,200,794 B1 * | 3/2001 | Whitehead et al. ............ | 435/232 |
| 6,271,018 B1 * | 8/2001 | Brash et al. ................ | 435/252.3 |
| 6,780,621 B2 * | 8/2004 | Whitehead et al. ............ | 435/136 |
| 7,037,693 B2 * | 5/2006 | Brash et al. .................... | 435/147 |
| 7,154,022 B2 * | 12/2006 | Howe et al. ................... | 800/281 |
| 8,017,386 B2 * | 9/2011 | Howe et al. ................ | 435/320.1 |
| 8,501,452 B2 * | 8/2013 | Bruhlmann et al. ......... | 435/232 |
| 2002/0142407 A1 | 10/2002 | Whitehead et al. ........... | 435/146 |
| 2005/0108791 A1 * | 5/2005 | Edgerton ...................... | 800/284 |
| 2007/0039069 A1 * | 2/2007 | Rogers et al. ................ | 800/281 |
| 2008/0139397 A1 | 6/2008 | Chodorge et al. ................. | 506/8 |
| 2009/0100536 A1 * | 4/2009 | Adams et al. ................ | 800/260 |
| 2009/0158452 A1 * | 6/2009 | Johnson et al. ............... | 800/260 |
| 2011/0214199 A1 * | 9/2011 | Coffin ........................... | 800/275 |
| 2011/0252501 A1 * | 10/2011 | Abad et al. .................... | 800/275 |

FOREIGN PATENT DOCUMENTS

| | | |
|---|---|---|
| EP | 1 080 205 B1 | 3/2001 |
| WO | WO 99/58648 A2 | 11/1999 |
| WO | WO 00/09679 A1 | 2/2000 |
| WO | WO 00/61740 A1 | 10/2000 |
| WO | WO 01/94606 A2 | 12/2001 |
| WO | WO 2006/003298 A2 | 1/2006 |

OTHER PUBLICATIONS

Matsui, K., et al., 1996, "Bell pepper fruit fatty acid hydroperoxide lyase is a cytochrome P450 (CYP74B)", FEBS Letters, vol. 394, No. 1, pp. 21-24.*

Bate, N. J., et al., 1998, "Molecular characterization of an *Arabidopsis* gene encoding hydroperoxide lyase, a cytochrome P-450 that is wound inducible", Plant Physiology, vol. 117, pp. 1393-1400.*

Matsui, K., et al., 2000, "Fatty acid hydroperoxide lyase in tomato fruits: Cloning and properties of a recombinant enzyme expressed in *Escherichia coli*", Bioscience, Biotechnology and Biochemistry, vol. 64, pp. 1189-1196.*

Gomi K., et al., 2003, "Characterization of a hydroperoxide lyase gene and effect of C6-volatiles on expression of genes of the oxylipin metabolism in citrus", Journal of Plant Physiology, vol. 160, pp. 1219-1231.*

Wu, Z., and Burns, J.., 2003, "Molecular cloning and expression of fatty acid hydroperoxide lyase gene isolated from orange leaf", UniProt Accession No. Q84V86_CITSI. Provided as a PDF with the first communication on the merits.*

International Search Report and the Written Opinion of the International Searching Authority, application No. PCT/IB2008/052539, mailed Nov. 7, 2008.

Altschul et al., "Gapped BLAST and PSI-BLAST: a new generation of protein database search programs," Nucleic Acids Research, vol. 25, No. 17, pp. 3389-3402 (1997).

Amann et al., "Tightly regulated tac promoter vectors useful for the expression of unfused and fused proteins in *Escherichia coli*," Gene, vol. 69, pp. 301-315 (1988).

Baldari et al., "A novel leader peptide which allows efficient secretion of a fragment of human interleukin 1β in *Saccharamyces cerevisiae*," The EMBO Journal, vol. 6, No. 1, pp. 229-234 (1987).

Becker et al., "New plant binary vectors with selectable markers located proximal to the left T-DNA border," Plant Molecular Biology, vol. 20, pp. 1195-1197 (1992).

(Continued)

*Primary Examiner* — Manjunath Rao
*Assistant Examiner* — William W Moore

(57) ABSTRACT

Fatty acid 13-hydroperoxide lyase proteins which have been modified with respect to a previously described guava 13-hydroperoxide lyase and the nucleic acid sequences encoding these proteins. Also, recombinant nucleic acid molecules for expressing the modified 13-hydroperoxide lyases and methods of using such lyases in the field of organic synthesis.

5 Claims, 2 Drawing Sheets

(56) References Cited

OTHER PUBLICATIONS

Becker et al., "Amplified Expression of Fructose 1,6-Bisphosphatase in *Corynebacterium glutamicum* Increases In Vivo Flux through Pentose Phosphate Pathway and Lysine Production on Different Carbon Sources," Applied and Environmental Microbiology, pp. 8587-8596 (2005).

Bevan, "Binary *Agrobacterium* vectors for plant transformation," Nucleic Acids Research, vol. 12, No. 22, pp. 8711-8721 (1984).

Falciatore et al., "Transformation of Nonselectable Reporter Genes in Marine Diatoms," Marine Biotechnology, vol. 1, pp. 239-251 (1999).

Follettie et al., "Gene Structure and Expression of the *Corynebacterium flavum* N13 *ask-asd* Operon," Journal of Bacteriology, vol. 175, No. 13, pp. 4096-4103 (1993).

Gottesman, "Minimizing Proteolysis in *Escherichia coli*: Genetic Solutions," Methods in Enzymology, vol. 185, pp. 119-129 (1990).

Greasham et al., "Design and optimization of growth media," Applied Microbial Physiology: A Practical Approach, edited by P. Malcolm Rhodes and Peter F. Stanbury, pp. 53-74 (1997).

Gruber et al., "Vectors for Plant Transformation," Methods in Plant Molecular Biology and Biotechnology, edited by Bernard R. Gliek, Chapter 7, pp. 89-119 (1993).

Hatanaka et al., "Biosynthetic Pathway for $C_6$-Aldehydes Formation from Linolenic Acid in Green Leaves," Chemistry and Physics of Lipids, vol. 44, pp. 341-361 (1987).

Hatanaka "The Biogeneration of Green Odour by Green Leaves," Phytochemistry, vol. 34, No. 5, pp. 1201-1218 (1993).

Hellens et al., "A Guide to *Agrobacterium* Binary Ti Vectors," Trends in Plant Science., vol. 5, No. 10, pp. 446-451 (2000).

Koeduka et al., "Cloning of Lipoxygenase Genes from a Cyanobacterium, *Nostoc punctiforme*, and its Expression in *Eschelichia coli*," Current Microbiology, Vo. 54, pp. 315-319 (2007).

Kurjan et al., "Structure of a Yeast Pheromone Gene (MFα): A Putative α-Factor Precursor Contains Four Tandem Copies of Mature α-Factor," Cell, vol. 30, pp. 933-943 (1982).

Lang et al., "Oxylipin formation in *Nostoc punetiforme* (PCC73102)," Phytochemistry, vol. 68, pp. 1120-1127 (2007).

Liebl et al., "Requirement of chelating compounds for the growth of *Corynebacterium glutamicam* in synthetic media," Applied Microbiology and Biotechnology, vol. 32, pp. 205-210 (1989).

Noordermeer et al., "Characterization of three cloned and expressed 13-hydroperoxide lyase isoenzymes from alfalfa with unusual N-terminal sequences and different enzyme kinetics," European Journal of Biochemistry, vol. 267, pp. 2473-2482 (2000).

Schäffer et al., "Improving the accuracy of PSI-BLAST protein database searches with composition-based statistics and other refinments," Nucleic Acids Research, vol. 29, No. 14, pp. 2994-3005 (2001).

Schultz et al., "Expression and secretion in yeast of a 400-kDa envelope glycoprotein derived from Epstein-Barr virus," Gene, vol. 54, pp. 113-123 (1987).

Smith et al., "Single-step purification of polypeptides expressed in *Escherichia coli* as fusions with glutathione S-transferase," Gene, vol. 67, pp. 31-40, (1988).

Studier et al., "Use of T7 RNA Polymerase to Direct Expression of Cloned Genes," Methods in Enzymolgy, vol. 185, pp. 60-89 (1990).

Tijet et al., "Purification, Molecular Cloning, and Expression of the Gene Encoding Fatty Acid 13-Hydroperoxide Lyase from Guava Fruit (*Psidium guajava*)," Lipids, vol. 35, No. 7, pp. 709-720, (2000).

White, "Vectors for Gene Transfer in Higher Plants," Transgenic Plants, vol. 1, pp. 15-48 (1993).

van den Hondel et al., "Gene transfer systems and vector development for filamentous fungi," Applied Molecular Genetics of Fungi (1991).

Yoshihama et al., "Cloning Vector System for *Corynebacterium glutamicum*," Journal of Bacteriology, vol. 162, No. 2, pp. 591-597 (1985).

"Expression of Cloned Genes in *Escherichia coli*," Molecular Cloning, Third Edition, Chapter 15, edited by Joseph Sambrook and David W. Russell, Cold Spring Harbor Laboratory Press, Cold Spring Harbor, NY (2001).

"Introducing Cloned Genes into Cultured Mammalian Cell," Molecular Cloning, Third Edition, Chapter 16, edited by Joseph Sambrook and David W. Russell, Cold Spring Harbor Laboratory Press, Cold Spring Harbor, NY (2001).

Wu et al., Genbank Accession No. Q84V86 (Jun. 1, 2003).

* cited by examiner

Figure 1

```
                  10         20         30         40         50         60         70         80         90        100
         ....|....|....|....|....|....|....|....|....|....|....|....|....|....|....|....|....|....|....|....|
SH34GC7   LPLKPIPGSYGWPLLGPTLDRLDYFWQGPETFFRKRIEKYKSTVFRANVPPCFPFFSNVNPNVVVVLDCESFAHLFDMEIVEKSNVLVGDFMPSVKYTG
SH34E8B   LPLKPIPGSYGWPLLGPISDRLDYFWFQGPETFFRKRIEKYKSTVFRANVPPCFPFFSNVNPNVVVVLDCESFAHLFDMEIVEKSNVLVGDFMPSVKYTG
SH33AC5   LPLKPIPGSYGWPLLGPILDRLDYFWFQGPETFFRKRIEKYKSTVFRANVPPCFPFFSNVNPNVVVVLDCESFAHLFDMEIVEKSNVLVGDFMPSVKYTG
SH33C2A   LPLKPIPGSYGWPLLGPISDRLDYFWFQGPETFFRKRIEKYKSTVFRANVPCFPFFSNVNPNVVVVLDCESFAHLFDMEIVEKSNVLVGDFMPSVKYTG
SH33B7A   LPLKPIPGSYGWPLLGPILDRLDYFWFQGPETFFRKRIEKYKSTVFRANVPCFPFFSNVNPNVVVVLDCESFAHLFDMEIVEKSNVLVGDFMPSVKYTG
SH30D10A  LPLKPIPGSYGWPLLGPISDRLDYFWFQGPETFFRKRIEKYKSTVFRANVPCFPFFSNVNPNVVVVLDCESFAHLFDMEIVEKSNVLVGDFMPSVKYTG
SH324E10  LPLKPIPGSYGWPLLGPILDRLDYFWFQGPETFFRKRIEKYKSTVFRANVPCFPFFSNVNPNVVVVLDCESFAHLFDMEIVEKSNVLVGDFMPSVKYTG
SH329D3   LPLKPIPGSYGWPLLGPILDRLDYFWFQGPETFFRKRIEKYKSTVFRANVPCFPFFSNVNPNVVVVLDCESFAHLFDMEIVEKSNVLVGDFMPSVKYTG
Seq ID No. 1  LPVRTIPGSYGWPLLGPISDRLDYFWFQGPETFFRKRIEKYKSTVFRANVPCFPFFSNVNPNVVVVLDCESFAHLFDMEIVEKSNVLVGDFMPSVKYTG 110        120        130        140        150        160        170        180        190        200
         ....|....|....|....|....|....|....|....|....|....|....|....|....|....|....|....|....|....|....|....|
SH34GC7   NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA
SH34E8B   NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA
SH33AC5   NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA
SH33C2A   NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA
SH33B7A   NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA
SH30D10A  NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA
SH324E10  NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA
SH329D3   NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA
Seq ID No. 1  NIRVCAYLDTSEPQHAQVKNFAMDILKRSSKVWESEVISNLDTMWDTIESSLAKDGNASVIFPLQKFLFNFLSKSIIGADPAASPQVAKSGYAMLDRWLA 210        220        230        240        250        260        270        280        290        300
         ....|....|....|....|....|....|....|....|....|....|....|....|....|....|....|....|....|....|....|....|
SH34GC7   LQLLPTIHIGVLQPLVEIFLHSWAYPFALVSGDYNKLYQFIEKEGREAVERAKAEFGLTHQEAIHNLLFILGFNAFGGFSIFLPTLLSNILSDTTGLQDR
SH34E8B   LQLLPTIHIGVLQPLVEIFLHSWAYPFALVSGDYNKLYQFIEKEGREAVERAKAEFGLTHQEAIHNLLFILGFNAFGGFSIFLPTLLSNILSDTTGLQDR
SH33AC5   LQLLPTIHIGVLQPLVEIFLHSWAYPFALVSGDYNKLYQFIEKEGREAVERAKAEFGLTHQEAIHNLLFILGFNAFGGFSIFLPTLLSNILSDTTGLQDR
SH33C2A   LQLLPTIHIGVLQPLVEIFLHSWAYPFALVSGDYNKLYQFIEKEGREAVERAKAEFGLTHQEAIHNLLFILGFNAFGGFSIFLPTLLSNILSDTTGLQDR
SH33B7A   LQLLPTIHIGVLQPLVEIFLHSWAYPFALVSGDYNKLYQFIEKEGREAVERAKAEFGLTHQEAIHNLLFILGFNAFGGFSIFLPTLLSNILSDTTGLQDR
SH30D10A  LQLLPTIHIGVLQPLVEIFLHSWAYPFALVSGDYNKLYQFIEKEGREAVERAKAEFGLTHQEAIHNLLFILGFNAFGGFSIFLPTLLSNILSDTTGLQDR
SH324E10  LQLLPTIHIGVLQPLVEIFLHSWAYPFALVSGDYNKLYQFIEKEGREAVERAKAEFGLTHQEAIHNLLFILGFNAFGGFSIFLPTLLSNILSDTTGLQDR
SH329D3   LQLLPTIHIGVLQPLVEIFLHSWAYPFALVSGDYNKLYQFIEKEGREAVERAKAEFGLTHQEAIHNLLFILGFNAFGGFSIFLPTLLSNILSDTTGLQDR
Seq ID No. 1  LQLLPTINIGVLQPLVEIFLHSWAYPFALVSGDYNKLYQFIEKEGREAVERAKAEFGLTHQEAIHNLLFILGFNAFGGFSIFLPTLLSNILSDTTGLQDR
```

Figure 1 (continued)

```
              310        320        330        340        350        360        370        380        390        400
              ....|....|....|....|....|....|....|....|....|....|....|....|....|....|....|....|....|....|....|....|
SH34GC7       LRKEVRAKGGPALSFASVKEMELVKSVVYETLRLNPPVPLQYARARKDFQLKSHDSVFDIKKGELLCGYQPLVMRDSKVFDDAESFKAERFMGEKGSELL
SH34E8B       LRKEVRAKGGPALSFASVKEMELVKSVVYETLRLNPPVPLQYARARKDFQLKSHDSVFDVKKGELLCGYQPLVMRDSKVFDDAESFKAERFMGEKGSELL
SH33AC5       LRKEVRAKGGPALSFASVKEMELVKSVVYETLRLNPPVPLQFARARKDFQLRSHDSVYDIKKGELLCGYQPLVMRDSKVFDDAESFKAERFMGEKGSELL
SH33C2A       LRKEVRAKGGPALSFASVKEMELVKSVVYETLRLNPPVPLQFARARKDFQLKSHDSVYEIKKGELLCGYQPLVMRDSKVFDDAESFKAERFMGEKGSELL
SH33B7A       LRKEVRAKGGPALSFASVKEMELVKSVVYETLRLNPPVPFQYARARKDFQLKSHDSVYDIKKGELLCGYQPLVMRDSKVFDDAESFKAERFMGEKGSELL
SH30D10A      LRKEVRAKGGPALSFASVKEMELVKSVVYETLRLNPPVPFQYARARKDFQLKSHDSVFDIKKGELLCGYQKVVMTDPKVFDEPESFNSDRFVQN--SELL
SH324E10      LRKEVRAKGGPALSFASVKEMELVKSVVYETLRLNPPVPLQFARARKDFQLSSYDSVYDIKKGELLCGYQPLVMRDSKVFDDAESFKAERFMGEKGSELL
SH329D3       LRKEVRAKGGPALSFASVKEMELVKSVVYETLRLNPPVPFQYARARKDFQLKSHDSVFDVKKGELLCGYQKVVMTDPKVFDEPESFNSDRFVQN--SELL
Seq ID No. 1

410        420        430        440        450
              ....|....|....|....|....|....|....|....|....|....|
SH34GC7       SYLYWSNGPQTGTPTESNKQCAAKDYVTLTACLFVAYMFRRYNSVTGSSSSITAVEKAK
SH34E8B       SYLYWSNGPQTGTPTESNKQCAAKDYVTLTACLFVAYMFRRYNSVTGSSSSITAVEKAK
SH33AC5       SYLYWSNGPQTGTPTESNKQCAAKDYVTLTACLFVAYMFRRYNSVTGSSSSITAVEKAK
SH33C2A       SYLYWSNGPQTGTPTESNKQCAAKDYVTLTACLFVAYMFRRYNSVTGSSSSITAVEKAK
SH33B7A       SYLYWSNGPQTGTPTESNKQCAAKDYVTLTACLFVAYMFRRYNSVTGSSSSITAVEKAN
SH30D10A      NYLYWSNGPQTGTPTESNKQCAAKDYVTLTACLFVAYMFRRYNSVTGSSSSITAVEKAN
SH324E10      SYLYWSNGPQTGTPTESNKQCAAKDYVTLTACLFVAYMFRRYNSVTGSSSSITAVEKAK
SH329D3       SYLYWSNGPQTGTPTESNKQCAAKDYVTLTACLFVAYMFRRYNSVTGSSSSITAVEKAN
Seq ID No. 1  DYLYWSNGPQTGTPTESNKQCAAKDYVTLTACLFVAYMFRRYNSVTGSSSSITAVEKAN
```

MODIFIED 13-HYDROPEROXIDE LYASES AND USES THEREOF

This application is a continuation application of application Ser. No. 12/664,565 which is a 371 filing of International Patent Application PCT/IB2008/052539 filed Jun. 25, 2008.

FIELD OF THE INVENTION

The present invention relates to fatty acid 13-hydroperoxide lyase proteins which have been modified with respect to a previously described guava 13-hydroperoxide lyase and the nucleic acid sequences encoding these proteins. The present invention also relates to means for expressing the modified 13-hydroperoxide lyases and methods of using such lyases in the field of organic synthesis.

BACKGROUND ART

Amongst the compounds which are useful in the perfume and flavor industry, involving hydroperoxide cleavage possibly carried out via enzymatic reaction, the so called "green notes" include n-hexanal, hexan-1-ol, 2-(E)-hexen-1-al, 2-(E)-hexen-1-ol, 3-(Z)-hexen-1-ol (also known as pipol) and 3-(Z)-hexen-1-al, which are widely used in flavors, particularly fruit flavors, to impart a fresh green character. Furthermore, green notes are essential for fruit aroma and are used extensively in the aroma industry. The demand for natural green notes has grown to exceed their supply from traditional sources such as mint (*Mentha arvensis*) oil. This has motivated research efforts toward finding alternative natural ways of obtaining these materials.

The synthesis of green note compounds starts from free (polyunsaturated) fatty acids such as linoleic (9-(Z), 12-(Z)-octadecadienoic) and a-linolenic (9-(Z), 12-(Z), 15-(Z)-octadecatrienoic) acids. In nature, these acids are released from cell membranes by lipolytic enzymes after cell damage. Fatty acid 13-hydroperoxides are formed by the action of a specific 13-lipoxygenase (13-LOX) and are subsequently cleaved by a specific 13-hydroperoxide lyase (13-HPOL) into a $C_6$ aldehyde and a $C_{12}$ ω-oxoacid moiety. The aldehydes can subsequently undergo thermal isomerization and/or be reduced by dehydrogenase enzymes to produce other $C_6$ products (i.e., green notes) such as alcohols (Hatanaka A. (1993) Phytochemistry 34: 1201-1218; Hatanaka A. et al. (1987) Chemistry and Physics of Lipids 44: 431-361).

Guava has been identified as an excellent source of freeze-stable 13-HPOL for use in this synthetic pathway. Guava 13-HPOL is currently used in an industrial process for the production of green notes (U.S. Pat. No. 5,464,761). In this process, a solution of the required 13-hydroperoxides is made from linoleic or linolenic acid (obtained from sunflower and linseed oils, respectively) using freshly prepared soybean flour as a source of 13-LOX. This solution is then mixed with a freshly prepared puree of whole guava (*Psidium guajava*) fruit as the source for 13-HPOL. The aldehyde products are then isolated by distillation. When the corresponding alcohols are required, fresh baker's yeast is added to the hydroperoxide solution before it is mixed with the guava puree. The yeast contains an active alcohol dehydrogenase enzyme that reduces the aldehydes to the corresponding alcohols as the aldehydes are formed by 13-HPOL.

There are a number of disadvantages to this industrial process. The principal disadvantage is the requirement of large quantities of fresh guava fruit. This means that the process has to be operated in a country where fresh guava fruit is cheaply and freely available. Even if such a site is found, availability is limited to the growing season of the fruit. Good quality guava fruit, for example, is only available for ten months of the year in Brazil.

A second disadvantage is that the desired enzyme activities are rather dilute in the sources employed. This means that relatively large amounts of soy flour (5%), guava puree (41%) and yeast (22%) have to be used in the process. The large volumes of these raw materials that are required for industrial production place physical constraints on the yields of green notes that can be achieved and raise the costs for the industrial process.

A third disadvantage is that it is a large-volume batch process, which, by its nature, does not make maximum use of the 13-HPOL enzyme's catalytic activity, is relatively labor-intensive and generates a large amount of residual organic material. The residual organic material must subsequently be transported to a compost farm or otherwise discarded.

To overcome some of the disadvantages of this industrial process, EP 1 080 205 discloses purified and recombinant guava 13-HPOL proteins, nucleic acids, expression systems, and methods of use thereof. However, upon using the recombinant guava 13-hydroperoxide lyase for producing $C_6$-aldehydes, it turned out that the yield of products obtained with the recombinant guava 13-hydroperoxide lyase could still be optimized.

Thus, there is still a strong interest in providing 13-HPOL enzymes which allow the recombinant expression of the enzyme and which can be used to obtain a high yield of the desired product.

The above mentioned objects of the invention are solved by the modified 13-hydroperoxide lyase polypeptides according to claim 1. Preferred embodiments are represented by the subject matter of the sub-claims.

SUMMARY OF THE INVENTION

The present invention provides a modified 13-hydroperoxide lyase polypeptide which comprises an amino acid sequence which has 1 to 40 amino acid alterations as compared to the amino acid sequence of the wild-type protein according to SEQ ID No. 1 and includes at least one amino acid alteration in a position selected from the group consisting of positions 3, 4, 5, 19, 208, 340, 342, 352, 354, 358, 359, 360, 371, 372, 375, 377, 382, 383, 387, 388, 389, 392, 393, 394, 395, 399 and 457 of the wild-type protein according to SEQ ID No. 1.

The present invention further provides an isolated nucleic acid molecule comprising a nucleotide sequence encoding a modified 13-hydroperoxide lyase of the present invention, recombinant nucleic acid molecules which allow the expression of the modified 13-hydroperoxide lyase in suitable host cells and transgenic cells comprising such recombinant nucleic acid molecules.

The present invention also provides a method for preparing a modified 13-hydroperoxide lyase polypeptide of the present invention by culturing one or more transgenic cells under conditions which permit expression of the polypeptide and optionally recovering the polypeptide.

The present invention is further directed to the use of the modified 13-hydroperoxide lyase of the present invention for cleaving a 13-hydroperoxide of a polyunsaturated fatty acid into an aldehyde and an oxocarboxylic acid.

Finally, the present invention provides a method of producing an aldehyde by providing a modified 13-hydroperoxide lyase according to the present invention, contacting a 13-hydroperoxide of a polyunsaturated fatty acid with the modified 13-hydroperoxide lyase and recovering the produced aldehyde or the corresponding alcohol after reduction of the aldehyde.

DETAILED DESCRIPTION OF THE INVENTION

The present invention relates to modified 13-hydroperoxide lyase polypeptides, nucleic acid molecules coding for said modified polypeptides, means for their expression and methods using the modified 13-hydroperoxide lyase.

The inventors have surprisingly found that introducing amino acid alterations into the amino acid sequence of guava 13-hydroperoxide lyase as disclosed in EP 1 080 205 by mutagenesis methods such as DNA shuffling and error prone PCR leads to modified enzymes with improved enzymatic activity as compared to the non-modified recombinant enzyme from guava. Furthermore, it has been found that the recombinant host cells which express the modified hydroperoxide lyase exhibit an excellent storage stability, i.e. they can be stored for several months, particularly if they are kept refrigerated. Another advantage of the present invention is that the modified enzymes show high initial reaction rates, which allow the production of a high quantity of product within a short period of time while using only low amounts of recombinant biomass. Furthermore, it is possible to re-use the modified enzymes in further reactions. Finally, it has been shown that the quality of the products obtained with the modified 13-hydroperoxide lyases of the present invention is superior to the existing products which are currently used for example in perfumery, as almost no isomerization occurs while the product is formed.

Within the meaning of the present invention, a "lyase" means a protein having at least one lyase function, i.e. the capability to catalyze the cleavage of a molecule. In particular, the term "13-hydroperoxide lyase" means that the lyase protein is capable of cleaving 13-hydroperoxides of polyunsaturated fatty acids. For example, the 13-hydroperoxide lyase is capable of cleaving a fatty acid 13-hydroperoxide of linoleic acid or linolenic acid into a $C_6$-aldehyde and a $C_{12}$-oxoacid moiety.

In terms of the invention, "modified" or "variant" means that the amino acid sequence of the modified or variant polypeptide is altered as compared to the amino acid sequence of the wild-type protein according to SEQ ID No. 1.

Modified 13-HPOL enzymes can be obtained by a person skilled in the art by different means such as DNA engineering including gene synthesis, site-directed mutagenesis, site-saturation mutagenesis and any other directed evolution technologies (random mutagenesis, shuffling, etc.) in which new DNA sequences are generated to create new variants (or libraries of new variants). This can be done from a single gene using random mutagenesis (WO 2006/003298). Diversity could also be generated from several parental genes using a family shuffling recombination step as described for instance in the WO 00/09679. Variants are then screened in order to select under stringent conditions the improved enzymatic activity. These improved variants can then be used in the next round of evolution. The amino acid sequence of the modified 13-hydroperoxide lyase has 1 to 40 amino acid alterations, preferably 5 to 35, also preferably 4 to 25, more preferably 6 to 25, even more preferably 10 to 30 and most preferably 17 to 25 amino acid alterations as compared to the amino acid sequence of the wild-type protein according to SEQ ID No. 1.

The term "wild-type protein" refers to the modified 13-hydroperoxide lyase enzyme as disclosed in EP 1 080 205, but with a deletion of 31 amino acids at the N-terminus compared to the sequence disclosed in EP 1 080 205. Enzymes carrying this deletion showed improved expression leading to a higher catalytic activity as compared to enzymes that do not show this deletion. The sequence of the wild-type protein according to the present invention is depicted in SEQ ID No. 1.

The term "amino acid alteration", as it is used herein, is intended to comprise an insertion of one or more amino acids between two amino acids, a deletion of one or more amino acids or a substitution of one or more amino acids with one or more different amino acids, as compared to the amino acid sequence of the wild-type protein as depicted in SEQ ID No. 1. The amino acid alterations can be easily identified by comparison of the amino acid sequence of the modified protein with the amino acid sequence of the wild-type protein.

Amino acid sequence comparisons may be performed using any of the variety of sequence comparison algorithms and programs known in the art. Such algorithms and programs include, but are by no means limited to BLASTP (Altschul et al. (1997) Nucl. Acids Res. 25: 3389-3402; Schäffer et al. (2001) Nucl. Acids Res. 29: 2994-3005) or BioEdit.

The term "position" refers to a specific amino acid residue present in the wild-type protein, as identified by a specific numbering of the amino acids. It is apparent to the expert that the insertion or deletion of one or more amino acid residues compared to the wild-type sequence leads to a different numbering between the wild-type amino acid sequence and the modified amino acid sequence. For example, if one amino acid is inserted between amino acids 299 and 300 of the wild-type amino acid sequence, the amino acid following the insertion will have the numbering 301 in a modified amino acid sequence, while it retains the numbering 300 in the wild-type sequence.

The modified 13-hydroperoxyde lyase of the invention may comprise one or more substitutions selected from the group consisting of V3L, R4K, T5P, S19L, N208H, F340L, Y342F, K352R, K352S, H354Y, F358Y, D359E, V360I, K371P, V372L, T375R, P377S, E382D, P383A, N387K, S388A, D389E, V392M, Q393G, N394E, D399S, D399N and N457K.

The modified 13-hydroperoxide lyase of the present invention may comprise at least 3 of said substitutions, preferably at least 4, 5, 6, 7 or 8, more preferably at least 9, 10, 11, 12, 13 or 14, even more preferably at least 15, 16, 17 or 18 and most preferably 19, 20, 21, 22, 23, 24 or 25 substitutions with respect to the amino acid sequence of the wild-type protein according to SEQ ID No. 1.

Preferably, the modified 13-hydroperoxide lyase of the present invention may comprise at least the following substitutions: V3L, R4K, T5P and N208H, as compared to the wild-type protein. All the variants disclosed in the present application and showing an enhanced activity have these substitutions. For example, the variant D10A, which is disclosed in the present application, comprises these four substitutions, and the additional substitutions V360I and D399N, as compared to the wild-type protein.

The hydroperoxyde lyase of the invention may also comprise the insertion of amino acids K and G between positions 394 and 395 of the amino acid sequence of the wild-type protein. This insertion has the effect that the amino acid sequences modified by this insertion are two amino acids longer than amino acid sequences which do not comprise this insertion. Furthermore, any additional mutations following the insertion will have a different numbering in the wild-type and the modified amino acid sequence. For example, amino acid residue 399 of the wild-type sequence corresponds to amino acid residue 401 in the modified sequence due to the insertion.

The modified 13-hydroperoxide lyase of the present invention may further comprise the following substitutions: K371P, V372L, T375R, P377S, E382D, P383A, N387K, S388A, D389E, V392M, Q393G, N394E, D399S.

Further examples of the 13-hydroperoxide lyase of the invention, designated GC7, E8B, B7A, C2A, AC5, 4E10 and 9D3, have different combinations of amino acid alterations as compared to the amino acid sequence of the wild-type protein. The variant GC7 has 21 amino acid substitutions, the variant E8B has 19 amino acid substitutions, the variant AC5 has 24 amino acid substitutions, the variant C2A has 22 amino acid substitutions, the variant B7A has 21 amino acid substitutions, the variant 4E10 has 15 amino acid substitutions and 9D3 has 25 amino acid substitutions as compared to the amino acid sequence of the wild-type protein according to SEQ ID No. 1. These seven variants have the substitutions V3L, R4K, T5P and N208H, as well as the substitutions K371P, V372L, T375R, P377S, E382D, P383A, N387K, S388A, D389E, V392M, Q393G, N394E and D399S, as compared to the amino acid sequence of the wild-type protein according to SEQ ID No. 1. Moreover, these variants all additionally have the insertion of amino acids K and G between positions 394 and 395 of the amino acid sequence of the wild-type protein. All positions given herein refer to the position in the amino acid sequence of the wild-type protein, unless stated otherwise.

Variant GC7 additionally comprises the amino acid substitutions S19L, F340L, V360I and N457K. Variant E8B additionally comprises the amino acid substitutions F340L and N457K. Variant AC5 additionally comprises the amino acid substitutions S19L, F340L, Y342F, K352R, F358Y, V360I and N457K. Variant C2A additionally comprises the amino acid substitutions F340L, Y342F, F358Y, D359E and V360I. Variant B7A additionally comprises the amino acid substitutions S19L, F358Y, V360I and N457K. Variant 4E10 additionally comprises the amino acid substitution V360I. Variant 9D3 additionally comprises the amino acid substitutions S19L, F340L, Y342F, K352S, H354Y, F358Y, V360I and N457K.

All the isolated variants exemplified (D10A, GC7, E8B, B7A, C2A, AC5, 4E10 and 9D3) additionally include the amino acid sequence ATPSSSSPE (SEQ ID NO:18) on the N-terminal end which results in an increased activity as compared to enzymes that do not have this insertion. This additional amino acid sequence is derived from 9-hydroperoxide lyase of *Cucumis melo* (U.S. Pat. No. 7,037,693) and is located at amino acid positions 1 to 9 of the sequences according to SEQ ID Nos. 2, 4, 6, 8, 10, 12, 14 and 16. The expert is aware that the insertion of the amino acid sequence leads to a different numbering between the wild-type and the variant proteins. For example, the amino acid at position 3 of the wild-type protein corresponds to the amino acid at position 12 of the variant.

Most preferably, the modified 13-hydroperoxide lyase according to the present invention has an amino acid sequence selected from the group consisting of SEQ ID Nos. 2 (variant GC7), 4 (variant E8B), 6 (variant AC5), 8 (variant C2A), 10 (variant B7A), 12 (variant D10A), 14 (variant 4E10) and 16 (variant 9D3).

The modified 13-hydroperoxide lyase enzymes of the present invention show an increased enzymatic activity compared to the wild-type 13-hydroperoxide lyase according to SEQ ID No. 1. The increase in activity is at least 10% or 20%, preferably 30% or 40%, also preferably at least 50% or 80%, especially preferably at least 100% or 200%, also especially preferably an increase at least by a factor of 5, 7 or 9, particularly preferably an increase at least by a factor of 10 or 20, also particularly preferably at least by a factor of 50 or 80, and most preferably at least by a factor of 100. The term "improved enzymatic activity" refers to the capability of the modified enzyme to lead to a higher yield factor than the wild-type enzyme. By "yield factor" it is understood here the ratio between the product concentration obtained and the concentration of biocatalyst (for example, purified recombinant enzyme or an extract from the host cells or the recombinant cells expressing the enzyme) in the reaction medium. The present inventors have shown that the modified 13-hydroperoxide lyases of the present invention lead to a 100% conversion of the substrate 13-hydroperoxy-octadecatrienoic acid, while the wild-type 13-hydroperoxide lyase from guava is only able to convert about 30% of the same substrate even at a high concentration of cells.

The 13-hydroperoxide lyase activity can be determined by incubating the purified enzyme or extracts from host cells or a complete host organism with a 13-hydroperoxide of a polyunsaturated fatty acid such as linolenic acid under appropriate conditions and analysis of the reaction products, e.g. by gas chromatography or HPLC analysis. Details about enzyme activity assays and analysis of the reaction products are given below in the examples.

The present invention further relates to isolated nucleic acid molecules comprising a nucleotide sequence encoding a modified 13-hydroperoxide lyase of the present invention. The expert is aware of the fact that due to the degeneracy of the genetic code a specific amino acid sequence may be encoded by different nucleic acid sequences. The invention is intended to comprise all nucleotide sequences which code for the 13-hydroperoxide lyases of the present invention.

Preferably, the nucleotide sequence coding for the modified 13-hydroperoxide lyase of the present invention is selected from the group consisting of SEQ ID Nos. 3, 5, 7, 9, 11, 13, 15 and 17, coding for the protein variants GC7, E8B, AC5, C2A, B7A, D10A, 4E10 and 9D3, respectively.

An "isolated" nucleic acid molecule is separated from other nucleic acid molecules present in the natural repository of nucleic acids. The nucleic acid molecules of the present invention, such as a nucleic acid molecule with a nucleotide sequence of Nos. 3, 5, 7, 9, 11, 13, 15 or 17 or a part thereof, can be isolated or produced using standard molecular biological techniques and the sequence information provided herein.

The present invention further relates to recombinant nucleic acid molecules comprising a nucleotide sequence of the present invention.

In terms of the invention, "transgenic" or "recombinant" means, with regard to e.g. a nucleic acid sequence, an expression cassette (=gene construct), or a vector containing the nucleic acid sequence according to the invention, or an organism transformed with the respective nucleic acid sequences, expression cassettes, or vectors, all of those constructs being produced by means of genetic technologies, that either
a) the nucleic acid sequence according to the invention, or
b) a genetic control sequence functionally linked to the nucleic acid sequence according to the invention, such as a promoter, or
c) a) and b)
is not in its natural genetic environment, or has been modified by genetic techniques, the modification being, for example, a substitution, addition, deletion, inversion, or insertion of one or several nucleotide residues. Natural genetic environment means the natural genomic or chromosomal locus in the parental organism, or the existence in a genomic library.

Another aspect of the invention pertains to organisms or host cells into which a recombinant expression vector of the invention has been introduced. The terms "host cell", "transgenic cell" and "recombinant cell" are used interchangeably herein. It is understood that such terms refer not only to the particular subject cell but also to the progeny or potential progeny of such a cell. Because certain modifications may occur in succeeding generations due to either mutation(s) or environmental influences, such progeny may not, in fact, be identical to the parent cell, but are still included within the scope of the term as used herein.

Host cells for expressing the nucleic acids, expression cassettes and vectors of the invention include bacteria, yeast, fungi, plant cells, plants, insect cells and mammalian cells.

It is obvious to the person skilled in the art that the nucleic acid sequence which encodes a 13-HPOL and which is used for the production of the transgenic cell may have to be adjusted to the organism specific codon usage. The codon usage can be determined with computer analyses of other known genes of the selected organism.

After their insertion into a cell, the nucleic acids used in the method can either be located on a separate plasmid, or advantageously be integrated into the genome of the host cell. In the case of integration into the genome, the integration can occur randomly, or by means of such a recombination that the native gene is replaced by the inserted copy, which causes the modulation of cellular 13-HPOL expression, or by using a gene in trans so that the gene is functionally linked to a functional expression unit which contains at least one sequence ensuring the expression of a gene, and at least one sequence ensuring the polyadenylation of a functionally transcribed gene.

In addition to the nucleic acid sequence coding for the 13-HPOL to be transferred, the recombinant nucleic acid molecules which are used for the expression of the 13-HPOL further comprise regulatory elements. Which precise regulatory elements these vectors have to contain depends in each case on the process in which these vectors are to be used. The person skilled in the art knows which regulatory and other elements a recombinant nucleic acid molecule has to contain.

Typically, the regulatory elements which are part of the vectors are such that allow for the transcription and, if desired, for the translation in the bacterial cell, yeast cell, insect cell, mammalian cell or plant cell. Depending on the organism selected, this can mean, for example, that the gene is only expressed and/or overexpressed after induction, or that it is expressed and/or overexpressed immediately. For example, these regulatory sequences are sequences to which inductors or repressors bind, thereby regulating the expression of the nucleic acid. In addition to these new regulatory sequences, or instead of these sequences, the natural regulation of the sequences upstream of the actual structural genes may still be existent, and may possibly have been genetically modified so that the natural regulation is disabled, and the expression of the genes is increased. The recombinant nucleic acid molecule, however, can also be constructed in a simpler manner, i.e. no additional regulation signals are inserted upstream of the nucleic acid sequence, and the natural promoter with its regulation has not been removed. Instead, the natural regulatory sequence has been mutated in such a manner that regulation no longer occurs, and/or gene expression is increased. To increase the activity, these altered promoters can also be inserted singly, in the form of partial sequences, upstream of the natural gene. Furthermore, the gene construct can also advantageously contain one or more so-called enhancer sequences which are functionally linked to the promoter, and which allow an increased expression of the nucleic acid sequence. Additional useful sequences, such as additional regulatory elements or terminators, can also be inserted at the 3' end of the DNA sequences.

In principle, it is possible to use any of the natural promoters with their regulation sequences for the method according to the invention. However, it is also possible and advantageous to use synthetic promoters only or in addition.

The vectors according to the invention, as the regulatory elements, can additionally comprise, e.g. enhancer elements. They may also contain resistance genes, replication signals, and additional DNA regions, which enable propagation of the vectors in bacteria, such as *E. coli*. The regulatory elements also comprise sequences which effect a stabilization of the vectors in the host cells. Such regulatory elements particularly comprise sequences facilitating stable integration of the vector into the host genome, or an autonomous replication of the vector in the cells. Such regulatory elements are known to the person skilled in the art.

The so-called termination sequences are sequences which ensure the proper termination of transcription or translation. If the transferred nucleic acids are to be translated, the termination sequences are typically stop codons and respective regulatory sequences; if the transferred nucleic acids are only to be transcribed in eukaryotes, they are generally poly(A) sequences.

As used herein, the term "vector" relates to a recombinant nucleic acid molecule which can transport another nucleic acid, to which it is bound, into a cell. A vector type is a "plasmid" representing a circular double stranded DNA loop, into which additional DNA segments can be ligated. Another vector type is a viral vector, wherein additional DNA segments can be ligated into the viral genome. Certain vectors can replicate autonomously in a host cell into which they have been inserted (e.g. bacterial vectors with a bacterial replication origin). Other vectors are advantageously integrated into the genome of a host cell when inserted in the host cell, and thereby replicated together with the host genome. Also, certain vectors can control the expression of genes to which they are functionally linked. These vectors are called here "expression vectors.". Usually, expression vectors suitable for DNA recombination techniques are of the plasmid type. In the present description "plasmid" and "vector" can be used interchangeably, since the plasmid is the vector type most often used. However, the invention is also intended to comprise other types of expression vectors, such as viral vectors which fulfil similar functions. Furthermore, the term "vector" is also intended to comprise other vectors known to the person skilled in the art, such as phages, viruses, such as SV40, CMV, TMV, transposons, IS elements, phasmids, phagemids, cosmids, linear or circular DNA.

In a recombinant expression vector, the term "operatively linked thereto" or "functionally linked thereto" means that the nucleotide sequence of interest is linked to the regulatory sequence(s) in such a way that the expression of the nucleotide sequence is possible, and that both sequences are linked to each other in such a way so as to fulfil the predicted function ascribed to the sequence.

The term "regulatory sequence" is intended to comprise promoters, enhancers, and other expression control elements (e.g. polyadenylation signals). These regulation sequences are described e.g. in Goeddel: Gene Expression Technology: Methods in Enzymology 185, Academic Press, San Diego, Calif. (1990), or in Gruber and Crosby, in: Methods in Plant Molecular Biology and Biotechnology, CRC Press, Boca Raton, Fla., publisher: Glick and Thompson, Chapter 7, 89-108. Regulatory sequences comprise those sequences which regulate the constitutive expression of a nucleotide sequence in many types of host cells, and those sequences which regulate the direct expression of the nucleotide sequence only in certain host cells under certain conditions.

The person skilled in the art knows that the design of the expression vector can depend on factors, such as the choice of the host cell to be transformed, the desired extent of the protein expression, etc.

The recombinant expression vectors used for the expression of the 13-HPOL can be active in both prokaryotic and eukaryotic cells. This is advantageous, since intermediate steps of the vector construction are often performed in microorganisms for the sake of simplicity. These cloning vectors contain a replication signal for the respective microorganism, and a marker gene for the selection of successfully transformed bacterial cells. Suitable vectors for expression in prokaryotic organisms are known to the person skilled in the art; they include e.g. *E. coli* pEXP5-NT/TOPO, pMAL series, pLG338, pACYC184, the pBR series, such as pBR322, the pUC series, such as pUC18, or pUC19, the M113mp series, pKC30, pRep4, pHS1, pHS2, pPLc236, pMBL24, pLG200, pUR290, pIN-III113-B1, λgt11, or pBdC1, *Streptomyces* pIJ101, pIJ364, 0.1702, or pIJ361, *Bacillus* pUB110, pC194, or pBD214, *Corynebacterium* pSA77, or pAJ667.

In another embodiment the expression vector represents a yeast expression vector or a baculovirus expression vector.

The above named vectors provide only a small overview of possible suitable vectors. Additional plasmids are known to the person skilled in the art and are described in e.g.: Cloning Vectors (publisher Pouwels, P. H. et al. Elsevier, Amsterdam, N.Y.-Oxford, 1985). For additional suitable expression systems for prokaryotic and eukaryotic cells see chapters 15 and 16 of Sambrook and Russell, vide supra.

In another embodiment of the method, the 13-HPOL can be expressed in single-celled plant cells (such as algae), see Falciatore et al. (1999) Marine Biotechnology 1(3): 239-251 and the literature cited therein, and in plant cells of higher plants (e.g. spermatophytes, such as crop plants). Examples for plant expression vectors comprise those extensively described in: Becker et al. (1992) Plant Mol. Biol. 20: 1195-1197; and Bevan (1984) Nucl. Acids Res. 12: 8711-8721; Vectors for Gene Transfer in Higher Plants; in: Transgenic Plants, Bd. 1, Engineering and Utilization, publisher: Kung and R. Wu, Academic Press, 1993, S. 15-38.

The gene to be expressed must, as described above, be functionally linked to a suitable promoter which regulates the gene expression in a time specific, cell specific or tissue specific manner.

In order to insert the 13-HPOL nucleotide sequence into the expression vectors, they are advantageously subjected to an amplification and ligation in the known manner. Preferably, one proceeds in accordance with the protocol of the Pfu DNA polymerase, or a Pfu/Taq DNA polymerase mixture. The primers are selected in accordance with the sequence to be amplified. Advantageously, the primer should be selected so that the amplified DNA comprises the entire codogenic sequence from the start codon to the stop codon. Advantageously, the amplified DNA is analyzed subsequent to the amplification. For example, the analysis can be made in respect of quality and quantity after gel electrophoretic separation. The amplified DNA can then be purified according to a standard protocol (e.g. Qiagen). An aliquot of the purified amplified DNA is then available for the subsequent cloning.

Suitable cloning vectors are generally known to the person skilled in the art. These particularly include vectors which are replicable in microbial systems, i.e. especially vectors which allow for an efficient cloning and expression in bacteria, yeasts or fungi, and/or which allow for the stable transformation of plants. Especially worth mentioning are various binary and co-integrated vector systems suitable for the T-DNA mediated transformation of plants. These binary vectors include vectors of the series pBIB-HYG, pPZP, pBecks, pGreen. According to the invention, Bin19, pBI101, pBinAR, pGPTV and pCAMBIA are preferred. An overview of binary vectors and their use is provided by Hellens et al. (2000) Trends in Plant Science 5: 446-451.

For the preparation of the vector, the vectors can initially be linearized by means of restriction endonuclease(s) and then enzymatically modified in any suitable way. The vector is then purified and an aliquot is used for cloning. During cloning the enzymatically cut and if necessary purified amplified DNA is linked to similarly prepared vector fragments by means of a ligase. A certain nucleic acid construct, or vector construct, or plasmid construct, may have one, or even several, codogenic gene regions. Preferably, the codogenic gene regions in these constructs are functionally linked to regulatory sequences as described above. The constructs can be advantageously cultivated in microorganisms, especially in *E. coli* and *Agrobacterium tumefaciens*, in a suitable medium, and stably propagated under selection conditions. The cells are then harvested and lysed and the plasmid is extracted therefrom. This allows a transfer of heterologous DNA into microorganisms or plants.

With the advantageous use of cloning vectors, the nucleic acids and the nucleic acid constructs according to the invention can be inserted into organisms, such as microorganisms, or plants, and used for plant transformation. The nucleic acids used in the method, the nucleic acids and nucleic acid constructs, and/or vectors according to the invention, can therefore be used for the genetic modification of a broad spectrum of organisms.

In terms of the invention, the term "transgenic cell" means, as described above, that the nucleic acids used in the method are not at their natural site in the genome of the cell, whereby the nucleic acids can expressed in homologous or heterologous host cells. However, transgenic also means that although the nucleic acids according to the invention are located at their natural site in the genome of an organism, i.e. the site of the 13-HPOL, the sequence has been changed compared to the natural sequence, and/or the regulatory sequences of the natural sequences have been modified. Preferably, transgenic is to be understood as the expression of the nucleic acids according to the invention at a non-natural site in the genome, i.e. the nucleic acids are homologously, or preferably heterologously expressed.

Host cells for expressing the nucleic acids, expression cassettes and vectors of the invention include bacteria, yeast, fungi, plant cells, plants, insect cells and mammalian cells.

Preferred host organisms according to the present invention are bacteria such as the ones of the genus *Escherichia*, fungi such as for example *Mortierella, Saprolegnia* or *Pythium,* yeasts such as *Saccharomyces*, cyanobacteria, ciliates, algae or protozoa such as dinoflagellates such as *Crypthecodinium.* Industrially used suitable microorganisms include, but are not limited to Gram negative bacteria such as *E. coli*, Gram positive bacteria such *B. subtilis*, fungi such as *A. niger, A. nidulans, N. crassa;* yeasts such as *S. cerevisiae, K. lactis, H. polymorpha, P. pastoris, Y. lipolytica;* actinomycetes such as *Streptomyces* sp. Several of these microorganisms are described in the 'Manual of Industrial Microbiology and Biotechnology' (editors in chief: A. L. Demain, J. E. Davies; ASM Press).

Further suitable host cells can be derived from: Goeddel, Gene Expression Technology: Methods in Enzymology 185, Academic Press, San Diego, Calif. (1990). Suitable expression strains, e.g. with a lower protease activity are described in: Gottesman, S., Gene Expression Technology: Methods in Enzymology 185, Academic Press, San Diego, Calif. (1990) 119-128.

Most preferably, E. coli cells are used. Suitable E. coli strains are, for example, MC1061, BL21, JM101, JM105, JM109 and DH5α.

According to the invention, the term "transgenic plant" comprises the plant in its entirety, as well as all parts of the plant in which the expression of the 13-HPOL proteins according to the invention is increased. This includes all parts of the plant and plant organs, such as leaf, stem, seed, root, tubers, anthers, fibers, root hair, stalk, embryos, calli, cotyledons, petioles, crop material, plant tissue, reproductive tissue, cell cultures derived from the transgenic plant, and/or which can be used to produce the transgenic plant.

The plants used for the method according to the invention can in principle be any plant which is to be made resistant to a pathogen infestation. Preferably, it is a monocotyledonous or dicotyledonous such as an agricultural plant, a food plant or a fodder plant.

Suitable mammalian cells include for example NIH3T3 cells, CHO cells, COS cells, 293 cells, Jurkat cells, BHK cells and HeLa cells.

The specific expression of the 13-HPOL protein in the transgenic cells according to the invention can be proven and tracked by means of common molecular biological and biochemical methods. The person skilled in the art knows these techniques and is easily able to select suitable detection methods, such as a Northern Blot analysis for the detection of 13-HPOL-specific RNA, or for the determination of the amount of accumulation of 13-HPOL-specific RNA, or a Southern Blot, or PCR, analysis for the detection of DNA sequences encoding the 13-HPOL. The probe or primer sequences used for this purpose can either be identical to the sequences given in SEQ ID Nos. 3, 5, 7, 9 11, 13, 15 or 17, or show some slight differences to these sequences.

If microorganisms are used in the present invention, these organisms are preferably grown under standard conditions in a fermentation process in a manner known to the expert.

The term "standard conditions" refers to the cultivation of a microorganism in a standard medium. The temperature, pH and incubation time can vary as described below.

The temperature should be usually in a range between 15° C. and 45° C., but the range may be higher, up to 105° C. for thermophilic organisms. The temperature can be kept constant or can be altered during the experiment.

The pH of the medium may be in the range of 5 to 8.5, preferably around 7.0, and can be maintained by the addition of buffers to the media. An exemplary buffer for this purpose is a potassium phosphate buffer. Synthetic buffers such as MOPS, HEPES, ACES and others can alternatively or simultaneously be used. It is also possible to maintain a constant culture pH through the addition of an acid or base, such as acetic acid, sulfuric acid, phosphoric acid, NaOH, KOH or $NH_4OH$ during growth. If complex medium components such as yeast extract are utilized, the necessity for additional buffers may be reduced, due to the fact that many complex compounds have high buffer capacities. If a fermentor is utilized for culturing the microorganisms, the pH can also be controlled using gaseous ammonia.

The incubation time is usually in a range from several hours to several days. This time is selected in order to permit the maximal amount of product to accumulate in the broth.

The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 ml or 250 shake flasks are used, filled with about 10% (by volume) of the required growth medium. The flasks should be shaken on a rotary shaker (amplitude about 25 mm) using a speed-range of about 100-300 rpm. Evaporation losses can be diminished by the maintenance of a humid atmosphere; alternatively, a mathematical correction for evaporation losses should be performed.

If genetically modified clones are tested, an unmodified control clone or a control clone containing the basic plasmid without any insert should also be tested.

The standard culture conditions for each microorganism used can be taken from the textbooks, such as Sambrook and Russell, Molecular Cloning—A laboratory manual, Cold Spring Harbour Laboratory Press, $3^{rd}$ edition (2001).

E.g., E. coli and C. glutamicum strains are routinely grown in MB or LB and BHI broth (Follettie, M. T. et al. (1993) J. Bacteriol. 175: 4096-4103, Difco Becton Dickinson). Usual standard minimal media for E. coli are M9 and modified MCGC (Yoshihama et al. (1985) J. Bacteriol. 162: 591-507; Liebl et al. (1989) Appl. Microbiol. Biotechnol. 32: 205-210.). Other suitable standard media for the cultivation of bacteria include NZCYM, SOB, TB, CG12 ½ and YT.

"Standard media" within the meaning of the present invention are intended to include all media which are suitable for the cultivation of the microorganisms of the present invention and include both enriched and minimal media.

"Minimal media" are media that contain only the minimal necessities for the growth of wild-type cells, i.e. inorganic salts, a carbon source and water.

In contrast, "enriched media" are designed to fulfil all growth requirements of a specific microorganism, i.e. in addition to the contents of the minimal media they contain for example growth factors.

Antibiotics may be added to the standard media in the following amounts (micrograms per milliliter): ampicillin, 50; kanamycin, 25; nalidixic acid, 25 to allow for the selection of transformed strains.

Suitable media consist of one or more carbon sources, nitrogen sources, inorganic salts, vitamins and trace elements. Preferred carbon sources are sugars, such as mono-, di-, or polysaccharides. For example, glucose, fructose, mannose, galactose, ribose, sorbose, lactose, maltose, sucrose, raffinose, starch or cellulose may serve as very good carbon sources.

It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates, urea, amino acids or complex nitrogen sources like corn steep liquor, soy bean flour, soy bean protein, yeast extract, meat extract and others.

Inorganic salt compounds which may be included in the media include the chloride, phosphate or sulfate salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include biotin, riboflavin, thiamin, folic acid, nicotinic acid, pantothenate and pyridoxin. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook "Applied Microbiol. Physiology, A Practical Approach (eds. P. M. Rhodes, P. F. Stanbury, IRL Press (1997) pp. 53-73, ISBN 0 19 963577 3). It is also possible to select growth media from commercial suppliers, like standard 1 (Merck) or BHI (brain heart infusion, DIFCO) or others.

Moreover, it may also be advantageous to add the heme precursor delta-aminolevulinic acid to the medium in order to improve the expression efficiency of active recombinant lyase.

All medium components should be sterilized, either by heat (20 minutes at 1.5 bar and 121° C.) or by sterile filtration. The components can either be sterilized together or, if necessary, separately.

The preparation of standard media used for the cultivation of bacteria usually does not involve the addition of single amino acids. Instead, in enriched media for use under standard culture conditions a mixture of amino acids such as peptone or trypton is added.

The transgenic cells according to the present invention can be cultivated in any suitable manner, for example by batch cultivation or fed-batch cultivation.

"Batch cultivation" within the meaning of the present invention is a cultivation method in which culture medium is neither added nor withdrawn during the cultivation.

A "fed-batch method" within the meaning of the present invention is a cultivation method in which culture medium is added during the cultivation, but no culture medium is withdrawn.

Expression of proteins in prokaryotes is most often carried out with vectors containing constitutive or inducible promoters directing the expression of either fusion or non-fusion proteins.

Fusion vectors add a number of amino acids to a protein encoded by the inserted nucleic acid sequence, usually to the amino terminus of the recombinant protein but also to the C-terminus or fused within suitable regions in the proteins. Such fusion vectors typically serve three purposes:
1) to increase expression of recombinant protein;
2) to increase the solubility of the recombinant protein; and
3) to aid in the purification of the recombinant protein by providing a ligand for affinity purification.

Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pQE (Qiagen), pGEX (Pharmacia Biotech Inc; Smith, D. B. and Johnson, K. S. (1988) Gene 67: 31-40), pMAL (New England Biolabs, Beverly, Mass.) and pRIT5 (Pharmacia, Piscataway, N.J.) which fuse glutathione 5-transferase (GST), maltose E binding protein, or protein A, respectively, to the recombinant protein.

Examples for *C. glutamicum* vectors can be found in the Handbook of *Corynebacterium* 2005 Eggeling, L. Bott, M., eds., CRC press USA.

Examples of suitable inducible non-fusion *E. coli* expression vectors include pTrc (Amann et al. (1988) Gene 69: 301-315), pLG338, pACYC184, pBR322, pUC18, pUC19, pKC30, pRep4, pHS1, pHS2, pPLc236, pMBL24, pLG200, pUR290, pIN-III113-B1, egtll, pBdC1, and pET lld (Studier et al., Gene Expression Technology: Methods in Enzymology 185, Academic Press, San Diego, Calif. (1990) 60-89; Pouwels et al., eds. (1985) Cloning Vectors. Elsevier: New York ISBN 0 444 904018). Target gene expression from the pTrc vector relies on host RNA polymerase transcription from a hybrid trp-lac fusion promoter. Target gene expression from the pET lld vector relies on transcription from a T7 gnlO-lac fusion promoter mediated by a coexpressed viral RNA polymerase (T7 gnl). This viral polymerase is supplied by host strains BL21 (DE3) or HMS174 (DE3) from a resident X prophage harboring a T7 gnl gene under the transcriptional control of the lacUV 5 promoter. For transformation of other varieties of bacteria, appropriate vectors may be selected. For example, the plasmids pIJ101, pIJ364, pIJ702 and pIJ361 are known to be useful in transforming *Streptomyces*, while plasmids pUB110, pC194, or pBD214 are suitable for transformation of *Bacillus* species. Several plasmids of use in the transfer of genetic information into *Corynebacterium* include pHM1519, pBL1, pSA77, or pAJ667 (Pouwels et al., eds. (1985) Cloning Vectors. Elsevier: New York IBSN 0 444 904018).

In another embodiment, the protein expression vector is a yeast expression vector. Examples of vectors for expression in yeast (*S. cerevisiae*) include pYepSecl (Baldari, et al. (1987) Embo J. 6: 229-234), 2i, pAG-1, Yep6, Yep13, pEM-BLYe23, pMFa (Kurjan and Herskowitz (1982) Cell 30: 933-943), pJRY88 (Schultz et al. (1987) Gene 54: 113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) in: Applied Molecular Genetics of Fungi, J. F. Peberdy, et al., eds., p. 1-28, Cambridge University Press: Cambridge, and Pouwels et al., eds. (1985) Cloning Vectors. Elsevier: New York (ISBN 0 444 904018).

Vector DNA can be introduced into prokaryotic cells via conventional transformation or transfection techniques. As used herein, the terms "transformation" and "transfection", "conjugation" and "transduction" are intended to refer to a variety of art-recognized techniques for introducing foreign nucleic acid (e. g., linear DNA or RNA (e. g., a linearized vector or a gene construct alone without a vector) or nucleic acid in the form of a vector (e.g., a plasmid, phage, phasmid, phagemid, transposon or other DNA into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (Molecular Cloning: A Laboratory Manual. 3rd ed., Cold Spring Harbor Laboratory, Cold Spring Harbor Laboratory Press, Cold Spring Harbor, N.Y., 2003), and other laboratory manuals.

In order to identify and select these integrants, a gene that encodes a selectable marker (e.g., resistance to antibiotics) is generally introduced into the host cells along with the gene of interest. Preferred selectable markers include those which confer resistance to drugs, such as, but not limited to, G418, hygromycin, kanamycin, tetracycline, neomycineampicillin (and other pencillins), cephalosporins, fluoroquinones, nalaxic acid, chloramphenicol, spectinomycin, erythromycin, streptomycin and methotrexate.

Other selectable markers include wild type genes that can complement mutated versions of the equivalent gene in a host or starting strain. For example, an essential gene for growth on a minimal medium, such as serA, can be mutated or deleted from the genome of a *C. glutamicum* starting or host strain of the invention as described herein above to create a serine auxotroph. Then, a vector containing a wild type or other functional copy of a serA gene can be used to select for transformants or integrants. Nucleic acid encoding a selectable marker can be introduced into a host cell on the same vector as that encoding the above-mentioned modified nucleic acid sequences or can be introduced on a separate vector. Cells stably transfected with the introduced nucleic acid can be identified by drug selection (e. g., cells that have incorporated the selectable marker gene will survive, while the other cells die).

When plasmids without an origin of replication and two different marker genes are used, it is also possible to generate marker-free strains which have part of the insert inserted into the genome. This is achieved by two consecutive events of homologous recombination (see also Becker et al. (2005) Appl. Environ. Microbiol. 71 (12): 8587-8596).

In another embodiment, recombinant microorganisms can be produced which contain selection systems which allow for regulated expression of the introduced gene. For example, inclusion of one of the above-mentioned nucleic acid sequences on a vector placing it under control of the lac operon permits expression of the gene only in the presence of IPTG. Such regulatory systems are well known in the art.

There are plurality of known techniques available for inserting DNA into a plant host cell, and the person skilled in the art will have no difficulty in finding the most suitable method in each case. These techniques comprise the transformation of plant cells with T-DNA using *Agrobacterium tumefaciens* or *Agrobacterium rhizogenes* as transformation agent, the fusion of protoplasts, the direct gene transfer of isolated DNA into protoplasts, the electroporation of DNA, the insertion of DNA by means of the biolistic method, as well as other possibilities. Both stable and transient transformants can be generated in this manner.

Of course, the plant cells containing the nucleic acid molecules according to the invention may also be further cultivated in the form of a cell culture (including protoplasts, calli, suspension cultures, and the like).

Besides using transgenic organisms or cells such as bacterial, yeast, insect, mammalian or plant cells and fungi or algae, the 13-HPOL enzymes of the present invention may also be expressed in a cell-free system using a suitable expression vector. The cell free expression is a coupled transcription and translation reaction to produce active recombinant protein in high amounts in vitro and can be obtained commercially.

The present invention further relates to a method for preparing a modified 13-hydroperoxide lyase polypeptide of the present invention by culturing one or more transgenic cells according to the present invention under conditions which permit expression of the polypeptide and optionally recovering the polypeptide.

The term "culturing of cells" means that the cells are grown under conditions that allow proliferation of the cells and expression of the polypeptide. These conditions include the medium containing components which are necessary for the metabolism of the cells, the temperature, the pH and the incubation time, as discussed above.

The polypeptide may be recovered by any purification method which is known in the art, e.g. gel filtration or chromatographic methods. Preferably, the protein is expressed as a fusion protein together with a number of amino acids which provide a ligand for affinity purification, such as glutathione S-transferase, maltose binding protein or protein A. As discussed above, these ligands may be removed after purification by treatment of the fusion protein with a protease.

The present invention further relates to the use of the modified 13-hydroperoxide lyase of the present invention for cleaving a 13-hydroperoxide of a polyunsaturated fatty acid into an aldehyde and an oxocarboxylic acid.

The term "polyunsaturated fatty acid" refers to fatty acids with at least two double bonds.

"Fatty acid hydroperoxides" are formed by oxidation of unsaturated fatty acids. In particular, 13-hydroperoxides are formed by the oxidation of unsaturated fatty acids at carbon atom 13. If linoleic acid or linolenic acid having 18 carbon atoms is used as the polyunsaturated fatty acid in the method of the present invention, the action of the 13-hydroperoxide lyase of the present invention leads to the production of a $C_6$-aldehyde and a C12-oxocarboxylic acid. For example, n-hexanal is produced from the 13-hydroperoxide of linoleic acid and 3-(Z)-hexen-1-al is produced from the 13-hydroperoxide of alpha-linolenic acid.

More particularly the reaction product obtained by cleavage of 13-hydroperoxydes of linseed oil hydrolysate (mixture of 13-hydroperoxydes of linoleic acid and of linolenic acid) by the 13 hydroperoxyde lyase of the invention is a mixture of n-hexanal, 3-(Z)-hexen-1-al and 2-(E)-hexen-1-al.

The $C_6$-aldehydes produced can then be used as flavour and/or fragrance ingredients or further reacted to yield other products such as the corresponding alcohols. The desired products obtained can be separated from the reaction medium by means of steam distillation and/or extraction with an inert organic solvent.

Therefore the present invention relates to a method of producing an aldehyde, comprising the steps of:
a) contacting a 13-hydroperoxide of a polyunsaturated fatty acid with the modified 13-hydroperoxide lyase of the present invention; and
b) recovering the produced aldehyde.

Preferably said method further comprises, prior to step a), the step of providing a modified 13-hydroperoxide lyase of the present invention.

Preferably the present invention relates to a method of producing a mixture of n-hexanal, 3-(Z)-hexen-1-al and 2-(E)-hexen-1-al, comprising the steps of
a) contacting a 13-hydroperoxyde of linseed oil hydrolysate with the modified 13-hydroperoxyde lyase of the invention; and
b) recovering the mixture of hexanal, 3-(Z)-hexen-1-al and 2-(E)-hexen-1-al produced in step a).

More preferably said method further comprises, prior to step a), the step of providing a modified 13-hydroperoxide lyase of the present invention.

The 13-hydroperoxide lyase of the present invention may be provided in different ways.

First, recombinant microbial cells (e.g. *E. coli*) may be lysed, e.g. by sonification, osmotic shock, freeze-thaw cycles or by the use of cell lysis kits (e.g. CelLytic™ of Sigma) and then the lysate obtained may be directly added to a solution of fatty acid hydroperoxides to form the aldehyde and the oxocarboxylic acid.

Second, the hydroperoxides may be produced in vivo in a transgenic cell or a transgenic organism such as microbial cells, plants, plant cell cultures, fungi, mammalian cells, insect cells and cyanobacteria.

Third, the 13-HPOL may be purified from the transgenic organism. Preferably, the nucleotide sequence coding for the 13-HPOL is cloned into a vector which contains a nucleotide sequence coding for an affinity tag such as cellulose binding protein, maltose binding protein, glutathione-S-transferase or a His-tag. After transcription and translation of the DNA a fusion protein is formed which can then be easily purified by means of affinity chromatography. Vectors and methods which are useful for the production and purification of the fusion protein are well-known to those skilled in the art. After the purification, the affinity tag may be removed by the action of a protease such as Factor X. However, such affinity tags provide increased activity of the recombinant fusion protein due to improved protein folding/solubility etc. These and other tags also allow the immobilisation of the fusion protein on cheap matrices such as amylose, cellulose, which can be used in reactors for the stabilization and recycling of the recombinant enzyme.

The term "contacting" means that the enzyme 13-hydroperoxide lyase and its substrate, the 13-hydroperoxide of a polyunsaturated fatty acid, are brought together under suitable reaction conditions to enable the reaction. The expert knows which reaction conditions have to be selected for the reaction to occur. Further, examples for such reaction conditions are given in the examples below.

The produced aldehyde can be recovered by any methods known to the expert, for example by means of steam distillation and/or extraction with an inert organic solvent. The reaction products can then be analyzed by means of gas chromatography or HPLC.

The substrate for the 13-hydroperoxide lyase, i.e. the 13-hydroperoxide of a polyunsaturated fatty acid, may be produced by the activity of a 13-lipoxygenase. Oxygenases catalyze the regio- and stereo specific dioxygenation of polyunsaturated fatty acids containing at least one 1-(Z), 4-(Z)-pentadiene system, e.g. linoleic acid, linolenic acid and arachidonic acid. 13-lipoxygenase has a specificity for the $C_{13}$-position within the fatty acid, i.e. it oxygenates preferably at carbon atom 13 of the hydrocarbon backbone of the fatty acid leading to 13-hydroperoxides of the fatty acid.

The 13-lipoxygenase may be provided in the form of homogenized soy beans which are the cheapest source of 13-lipoxygenase (see e.g. U.S. Pat. No. 5,464,761; U.S. Pat. No. 6,780,621). Another way to provide the 13-lipoxygenase is recombinant expression. The amino acid and nucleotide sequence of a prokaryotic lipoxygenase with $C_{13}$-specificity is disclosed in EP 06123710.3 and in Lang and Feussner (2007) Phytochemistry 68(8): 1120-1127 as well as in Koeduka et al. (2007) Curr. Microbiol. 54(4): 315-319. The recombinant 13-lipoxygenase may be produced in the same cell as the 13-hydroperoxide lyase or it may be produced in a separate cell. If it is produced within the same cell, the corresponding aldehydes may be produced from the hydroperoxides immediately after the latter are formed. The 13-lipoxygenase can be used in the form of a cell lysate, a cell suspension or of a purified protein as described above for the 13-hydroperoxide lyase.

The aldehydes produced by the method of the present invention may be reduced to their corresponding alcohols by various means, e.g. by adding fresh baker's yeast to the reaction solution. The yeast contains an active alcohol dehydrogenase enzyme that reduces the aldehyde. Alternatively, isolated alcohol dehydrogenases or chemical agents such as $KBH_4$ or $NaBH_4$ may be used for reducing the aldehyde to the corresponding alcohol.

The isolation of the variant 13-hydroperoxide lyases of the present invention and their characterization is described below in the examples. The following examples should not be construed as limiting. The content of all literature, patent applications, patents and published patent applications cited in this patent application is incorporated herein by reference.

EXAMPLES

Example 1

Molecular Evolution of Wild-Type Guava 13-hydroperoxide Lyase

The modified 13-hydroperoxide lyases of the present invention were obtained by several rounds of mutagenesis and shuffling of the DNA coding for the guava 13-hydroperoxide lyase according to SEQ ID No. 1 and additional DNA sequences coding for a 9-hydroperoxide lyase from *C. melo* and DNA sequences coding for 13-hydroperoxide lyases from *C. sinensis* and *N. attenuata*. The mutagenesis steps were performed by subjecting the DNA to the EvoSight™ method as described in WO 2006/003298. DNA shuffling steps were performed by subjecting the DNA to the L-Shuffling™ method as described in WO 00/09679. DNA coding for the guava 13-hydroperoxide lyase according to SEQ ID No. 1 was fragmented, mixed with fragmented additional DNA coding for a 9 or 13-hydroperoxide lyase from *C. melo, C. sinensis* and *N. attenuata* and reassembled through recursive steps of denaturation/hybridization on a matrix/ligation. High-throughput screening of the mutant proteins at each round of molecular evolution was done by monitoring the substrate consumption at 234 nm Identified improved variants were validated by chromatographic analysis of both the substrate and the products.

Example 2

Cloning of the Modified 13-hydroperoxide Lyases into Appropriate Expression Vectors The nucleotide sequences coding for the modified 13-hydroperoxy lyases GC7, E8B, AC5, C2A, B7A, D10A, E8B and 9D3 as depicted in SEQ ID Nos. 3, 5, 7, 9, 11, 13, 15 and 17, respectively, were cloned into the vector pMAL-c2X (New England Biolabs) by using a 5' linker containing an EcoRI site and a 3' linker containing a BamHI site. The list of the different plasmids obtained is shown in Table 1.

TABLE 1

Examples of recombinant plasmids

| Plasmid | Description |
|---------|-------------|
| pB7#A | EcoRI - BamHI fragment B7#A in pMAL-c2X |
| pAC#5 | EcoRI - BamHI fragment AC#5 in pMAL-c2X |
| pC2#A | EcoRI - BamHI fragment C2#A in pMAL-c2X |
| pE8#B | EcoRI - BamHI fragment E8#B in pMAL-c2X |
| pGC#7 | EcoRI - BamHI fragment GC#7 in pMAL-c2X |
| pD10#A | EcoRI - BamHI fragment D10#A in pMAL-c2X |
| p4E#10 | EcoRI - BamHI fragment 4E#10 in pMAL-c2X |
| p9D#3 | EcoRI - BamHI fragment 9D#3 in pMAL-c2X |
| pWT | EcoRI - BamHI DNA fragment coding for the protein of SEQ ID NO. 1 with an N-terminal insertion comprising the amino acids ATPSSSSPE (SEQ ID NO: 18) |

Example 3

Fatty Acid Hydroperoxide Cleavage by the Modified 13-hydroperoxide Lyases as Compared to the 'Wild-Type' Enzyme Experiment 1

E. coli MC1061 cells transformed with the plasmids pB7#A, pAC#5, pC2#A, pE8#B, pGC#7, p4E#10, p9D#3, pD10#A and pWT of Table 1 were cultivated in shake flask cultures in 25 ml of LB medium with 100 ppm of ampicillin at 180 rpm and at 20° C. for 30 hours without induction. Cultures were centrifuged and the pellet re-suspended in 100 mM phosphate buffer pH 7.6 and adjusted to an optical density of $OD_{600}=10$ for all transformed cells except those transformed with the plasmid pD10#A, for which the optical density was adjusted to $OD_{600}=25$. The catalytic activity of the 13-HPOL enzyme variants was determined as follows: 100 µl (10% v/v) of cell suspension ($OD_{600}=10$, respectively $OD_{600}=25$) were added to 900 µl of a solution containing 84.3 g $kg^{-1}$ of fatty acid hydroperoxides (including about 75% of the substrate 13-HPOT) previously produced with linseed oil hydrolysate as a source of fatty acids and ground soybeans as the source of the 13-lipoxygenase. 20 mg of horse liver alcohol dehydrogenase as reducing agent and 330 mg of NADH were added under stirring. The reaction was carried out at room temperature for 2 minutes. An aliquot of 100 µl of the reaction mixture was diluted with 900 µl of water, extracted with one volume of ethyl acetate and assayed by gas chromatography for the presence of 3-(Z)-hexen-1-ol. The consumption of the fatty acid hydroperoxides was followed by HPLC. The molar yield is expressed as the ratio between the amount of 3-(Z)-hexen-1-ol obtained during the reaction and the amount of 3-(Z)-hexen-1-ol one could theoretically obtain from the amount of 13-HPOT present in the reaction.

The results of this experiment are listed in Table 2, showing the improved enzymatic activity of the modified lyases compared to the recombinant wild-type enzyme (pWT).

TABLE 2

Activity of modified hydroperoxide lyases Soluble alcohol dehydrogenase from horse liver and NADH was used as the reducing agent.

| Plasmid | Biocatalyst concentration ($OD_{600}$) | 3-(Z)-hexen-1-ol (g $l^{-1}$) | Molar yield (%) | 13HPOT conversion (%) |
|---|---|---|---|---|
| pB7#A | 1 | 4.6 | 31 | 38 |
| pAC#5 | 1 | 4.0 | 27 | 38 |
| pC2#A | 1 | 5.3 | 35 | 43 |
| pE8#B | 1 | 4.8 | 32 | 44 |
| pGC#7 | 1 | 4.3 | 29 | 46 |
| p4E#10 | 1 | 3.9 | 26 | 40 |
| p9D#3 | 1 | 3.8 | 25 | 38 |
| pD10#A | 2.5 | 2.8 | 18.7 | 58 |
| pWT | 1 | 0.2 | 1.3 | <10* |

*within the analytical error margin

Experiment 2

E. coli MC1061 cells harboring the plasmids pB7#A, pAC#5, pC2#A, pE8#B, pGC#7, p4E#10, pD10#A, p9D3 and pWT of Table 1 were cultivated in shake flask cultures in 25 ml of LB medium containing 100 ppm of ampicillin at 180 rpm and at 20° C. for 30 hours without induction. Cultures were centrifuged and the pellet re-suspended in 100 mM phosphate buffer pH 7.6. The cell density was adjusted to an optical density of $OD_{600}=20$ for all transformed cells except those transformed with the plasmid pD10#A, for which the optical density was adjusted to $OD_{600}=10$. The catalytic activity was determined as follows: 100 µl (10% v/v) of cell suspension ($OD_{600}=20$, respectively $OD_{600}=10$) were added to 900 µl of a solution containing 84.3 g $kg^{-1}$ of fatty acid hydroperoxides (including about 75% of the substrate 13-HPOT) previously produced with linseed oil hydrolysate as a source of fatty acids and ground soybeans as the source of the 13-lipoxygenase. The reaction was carried out at room temperature for 5 minutes. An aliquot of 100 µl of the reaction was diluted in 900 µl of water containing 2-3 mg of the reducing agent $NaBH_4$ and stirred for 10 minutes. The reduced reaction mixture was extracted with one volume of ethyl acetate and assayed by gas chromatography for the presence of 3-(Z)-hexen-1-ol. The consumption of the fatty acid hydroperoxides was followed by HPLC. The molar yield is expressed as the ratio between the amount of 3-(Z)-hexen-1-ol obtained during the reaction and the amount of 3-(Z)-hexen-1-ol one could theoretically obtain from the amount of 13-HPOT present in the reaction.

The results of this experiment are listed in Table 3, showing the improved enzymatic activity of the modified lyases compared to the recombinant wild-type enzyme (pWT).

TABLE 3

Activity of modified hydroperoxide lyases $NaBH_4$ was used as the reducing agent.

| Plasmid | Biocatalyst concentration ($OD_{600}$) | 3-(Z)-hexen-1-ol (g $l^{-1}$) | Molar yield (%) | 13HPOT conversion (%) |
|---|---|---|---|---|
| pB7#A | 2 | 7.4 | 49 | 59 |
| pAC#5 | 2 | 7.9 | 53 | 54 |
| pC2#A | 2 | 9.7 | 65 | 55 |
| pE8#B | 2 | 8.8 | 59 | 65 |
| pGC#7 | 2 | 8.5 | 57 | 66 |
| p4E#10 | 2 | 6.4 | 43 | 54 |
| p9D#3 | 2 | 5.4 | 36 | 55 |
| pD10#A | 1 | 0.9 | 6 | N/D* |
| pWT | 2 | 0.8 | 5 | 29 |

*No Data

Experiment 3

E. coli MC1061 cells transformed with the plasmids pB7#A, pAC#5, pC2#A, pE8#B, pGC#7, pD10#A and pWT of Table 1 were cultivated in shake flask cultures in 100 ml of LB medium with 100 ppm of ampicillin at 180 rpm and at 20° C. for 30 hours without induction. Cultures were centrifuged, the pellet was re-suspended in 100 mM phosphate buffer pH 7.6 and the optical density was adjusted to $OD_{600}=10$. The catalytic activity was determined as follows: 500 mg of dried baker's yeast were added to 800 µl of 100 mM phosphate buffer at pH 7.6 and stirred for 30 seconds. 3.7 ml of a solution containing 83 g $kg^{-1}$ of fatty acid hydroperoxides previously produced (including about 75% of the substrate 13-HPOT) with linseed oil hydrolysate as a source of fatty acids and ground soybeans as the source of the 13-lipoxygenase were added. 500 µL (10% v/v) of recombinant cells of E. coli ($OD_{600}=10$) harboring the plasmid of interest were then rapidly added under stirring. The reaction was kept at room temperature for 1 hour. An aliquot of 100 µl of the reaction was diluted with 900 µl of water, extracted with 1 ml of ethyl acetate and assayed by gas chromatography for the presence of 3-(Z)-hexen-1-ol.

The results of this experiment are listed in Table 4, showing the improved enzymatic activity of the modified lyases of the present invention compared to the recombinant wild-type enzyme (pWT).

TABLE 4

Activity of modified hydroperoxide lyases
Baker's yeast served as the reducing agent.

| Plasmid | Biocatalyst concentration ($OD_{600}$) | 3-(Z)-hexen-1-ol ($g\,l^{-1}$) |
|---|---|---|
| pB7#A | 1 | 1.2 |
| pAC#5 | 1 | 1.2 |
| pC2#A | 1 | 1.5 |
| pE8#B | 1 | 1.1 |
| pGC#7 | 1 | 2.4 |
| pD10#A | 1 | 0.5 |
| pWT | 1 | 0.2 |

Experiment 4

E. coli MC1061 cells harboring the plasmids pGC#7, p9D#3, pD10#A and pWT of Table 1 were cultivated in shake flask cultures in 25 ml of LB medium containing 100 ppm of ampicillin at 180 rpm and at 20° C. for 30 hours without induction. Cultures were centrifuged and the pellet re-suspended in 100 mM phosphate buffer pH 7.6. Cell suspensions were prepared having different optical densities ranging between $OD_{600}=20$ to $OD_{600}=250$. The catalytic activity was determined as follows: 100 µl (10% v/v) of cell suspension ($OD_{600}=20$ to $OD_{600}=250$) were added to 900 µl of a solution containing 84.3 g $kg^{-1}$ of fatty acid hydroperoxides previously produced with linseed oil hydrolysate as a fatty acid source and ground soybeans as the source of the 13-lipoxygenase. The reaction was carried out at room temperature for 5 minutes. An aliquot of 10 µl of the reaction was diluted in 990 µl of ethanol and assayed for the consumption of 13HPOT by HPLC analysis. The results of this experiment are shown in FIG. 2. This experiment confirms that the modified 13-hydroperoxide lyases of the present invention lead to a 100% conversion of the substrate 13-hydroperoxy-octadecatrienoic acid, while the wild-type 13-hydroperoxide lyase from guava only converts about 30% of the 13-hydroperoxy-octadecatrienoic acid even at an $OD_{600}$ of 25.

Example 4

Performance of the Modified 13-hydroperoxide Lyase GC#7

Experiment 1

Cells of E. coli MC1061:pGC#7 were grown at 20° C. in 2 liter of LB medium containing 100 ppm of ampicillin in a stirred lab-scale reactor for 30 h. The culture was aerated with air at 1 vvm. Cells were harvested by centrifugation and re-suspended in 100 mM phosphate buffer pH 7.6 to yield an optical density of $OD_{600}=68$. Fatty acid hydroperoxides were produced with linseed oil hydrolysate as a source of fatty acids and ground soybeans as the source of the 13-lipoxygenase. 172 ml of recombinant E. coli cells MC1061:pGC#7 ($OD_{600}=68$) were added to 1544 g of fatty acid hydroperoxide solution containing 87 g $kg^{-1}$ of HPOT/D under stirring at room temperature. The reaction was stopped after 5 minutes by adding 50 ml of an aqueous solution containing 36% of the reducing agent NaBH4. 3-(Z)-hexen-1-ol was subsequently isolated by distillation under reduced pressure yielding 8.7 gram of 3-(Z)-hexen-1-ol.

Experiment 2

Cells of E. coli MC1061:pGC#7 were grown at 30° C. using a mineral salt medium containing 100 ppm of ampicillin. The pH was kept at pH 7 and the culture was aerated with air at 1 vvm. The gene expression was induced by adding 0.5 mM of IPTG at an $OD_{600}=4$. After 24 hours an optical density of $OD_{600}=9$ was reached. Cells were harvested by centrifugation and re-suspended in 100 mM of phosphate buffer of pH 7.6 to give an optical density of $OD_{600}=10$. 100 µl (10% v/v) of this cell suspension were added to 900 µl of a solution containing 83 g $kg^{-1}$ of fatty acid hydroperoxides previously produced with linseed oil hydrolysate as a fatty acid source and ground soybeans as the source of the 13-lipoxygenase. The reaction was carried out at room temperature for 5 minutes. An aliquot of 100 µl of the reaction mixture was diluted with 900 µl of water containing 2-3 mg of the reducing agent $NaBH_4$. The reduced reaction mixture was extracted with one volume of ethyl acetate and assayed by gas chromatography for the volatile $C_6$ alcohols. A concentration of 9.5 g $l^{-1}$ of 3-(Z)-hexen-1-ol was estimated to be produced by the recombinant MC1061:pGC7 in a reaction as described above.

BRIEF DESCRIPTION OF THE DRAWINGS

FIG. 1 shows an alignment of amino acid sequences of different modified 13-hydroperoxide lyases designated as GC7, E8B, B7A, C2A, AC5, D10A, 4E10 and 9D3 with the wild-type amino acid sequence according to SEQ ID No.1. The amino acid insertions and substitutions are shown in bold letters. The first 9 amino acids of variants GC7, E8B, B7A, C2A, AC5, D10A, 4E10 and 9D3 as depicted in SEQ ID Nos. 2, 4, 6, 8, 10, 12, 14 and 16 are not shown in the alignment, as they are derived from 9-hydroperoxide lyase and not from SEQ ID No. 1.

FIG. 2 shows the consumption of 13-HPOT at different cell densities of the E. coli clones expressing the variant or the wild-type 13-hydroperoxide lyase, respectively. pGC#7: circles; p9D#3: triangles; pD10#A: squares and pWT: diamonds.

What is claimed is:

1. A modified 13-hydroperoxide lyase polypeptide comprising an amino acid sequence which has no more than 40 amino acid alterations as compared to the amino acid sequence of the wild-type protein having the amino acid sequence of SEQ ID NO. 1 wherein at least one amino acid alteration position is selected from the group consisting of positions 3, 4, 5, 19, 208, 340, 342, 352, 354, 358, 359, 360, 371, 372, 375, 377, 382, 383, 387, 388, 389, 392, 393, 394, 395, 399 and 457, with said modified 13-hydroperoxide lyase having increased enzymatic activity as compared to the wild-type protein having the amino acid sequence of SEQ ID NO. 1 and wherein the modified lyase comprises one or more substitutions selected from the group consisting of V3L, R4K, T5P, S19L, N208H, F340L, Y342F, K352R, K352S, H354Y, F358Y, D359E, V360I, K371 P, V372L, T375R, P377S, E382D, P383A, N387K, S388A, D389E, V392M, Q393G, N394E, D399S, D399N and N457K wherein the modified polypeptide has the amino-terminal amino acid sequence ATPSSSSPE (SEQ ID NO:18).

2. A method for preparing a modified 13-hydroperoxide lyase polypeptide comprising:
culturing one or more transgenic cells transformed with a recombinant nucleic acid molecule comprising a nucleotide sequence encoding the modified 13-hydroperoxide lyase of claim 1 under conditions which permit expression of the polypeptide, and optionally recovering the polypeptide.

3. A method of producing an aldehyde, which comprises:
contacting a 13-hydroperoxide of a polyunsaturated fatty acid selected from the group consisting of linoleic acid or alpha-linolenic acid, with a modified 13-hydroperoxide lyase according to claim 1 to produce an aldehyde; and recovering the aldehyde.

4. The method according to claim 3, wherein the polyunsaturated fatty acid is linoleic acid or alpha-linolenic acid; and the method further comprises producing the 13-hydroperoxide by the activity of a 13-lipoxygenase.

5. The method according to claim 3, which further comprises reducing the aldehyde to the corresponding alcohol and optionally recovering the alcohol.

* * * * *

SEQUENCE LISTING

```
<160> NUMBER OF SEQ ID NOS: 18

<210> SEQ ID NO 1
<211> LENGTH: 457
<212> TYPE: PRT
<213> ORGANISM: Psidium guajava
<220> FEATURE:
<223> OTHER INFORMATION: 13-hydroperoxide lyase from Psidium guajava

<400> SEQUENCE: 1

Leu Pro Val Arg Thr Ile Pro Gly Ser Tyr Gly Trp Pro Leu Leu Gly
1               5                   10                  15

Pro Ile Ser Asp Arg Leu Asp Tyr Phe Trp Phe Gln Gly Pro Glu Thr
```

-continued

```
                  20                  25                  30
Phe Phe Arg Lys Arg Ile Glu Lys Tyr Lys Ser Thr Val Phe Arg Ala
                  35                  40                  45
Asn Val Pro Pro Cys Phe Pro Phe Ser Asn Val Asn Pro Asn Val
 50                  55                  60
Val Val Val Leu Asp Cys Glu Ser Phe Ala His Leu Phe Asp Met Glu
 65                  70                  75                  80
Ile Val Glu Lys Ser Asn Val Leu Val Gly Asp Phe Met Pro Ser Val
                  85                  90                  95
Lys Tyr Thr Gly Asn Ile Arg Val Cys Ala Tyr Leu Asp Thr Ser Glu
                 100                 105                 110
Pro Gln His Ala Gln Val Lys Asn Phe Ala Met Asp Ile Leu Lys Arg
                 115                 120                 125
Ser Ser Lys Val Trp Glu Ser Glu Val Ile Ser Asn Leu Asp Thr Met
                 130                 135                 140
Trp Asp Thr Ile Glu Ser Ser Leu Ala Lys Asp Gly Asn Ala Ser Val
145                 150                 155                 160
Ile Phe Pro Leu Gln Lys Phe Leu Phe Asn Phe Leu Ser Lys Ser Ile
                 165                 170                 175
Ile Gly Ala Asp Pro Ala Ala Ser Pro Gln Val Ala Lys Ser Gly Tyr
                 180                 185                 190
Ala Met Leu Asp Arg Trp Leu Ala Leu Gln Leu Leu Pro Thr Ile Asn
                 195                 200                 205
Ile Gly Val Leu Gln Pro Leu Val Glu Ile Phe Leu His Ser Trp Ala
                 210                 215                 220
Tyr Pro Phe Ala Leu Val Ser Gly Asp Tyr Asn Lys Leu Tyr Gln Phe
225                 230                 235                 240
Ile Glu Lys Glu Gly Arg Glu Ala Val Glu Arg Ala Lys Ala Glu Phe
                 245                 250                 255
Gly Leu Thr His Gln Glu Ala Ile His Asn Leu Leu Phe Ile Leu Gly
                 260                 265                 270
Phe Asn Ala Phe Gly Gly Phe Ser Ile Phe Leu Pro Thr Leu Leu Ser
                 275                 280                 285
Asn Ile Leu Ser Asp Thr Thr Gly Leu Gln Asp Arg Leu Arg Lys Glu
                 290                 295                 300
Val Arg Ala Lys Gly Gly Pro Ala Leu Ser Phe Ala Ser Val Lys Glu
305                 310                 315                 320
Met Glu Leu Val Lys Ser Val Val Tyr Glu Thr Leu Arg Leu Asn Pro
                 325                 330                 335
Pro Val Pro Phe Gln Tyr Ala Arg Ala Arg Lys Asp Phe Gln Leu Lys
                 340                 345                 350
Ser His Asp Ser Val Phe Asp Val Lys Lys Gly Glu Leu Leu Cys Gly
                 355                 360                 365
Tyr Gln Lys Val Val Met Thr Asp Pro Lys Val Phe Asp Glu Pro Glu
                 370                 375                 380
Ser Phe Asn Ser Asp Arg Phe Val Gln Asn Ser Glu Leu Leu Asp Tyr
385                 390                 395                 400
Leu Tyr Trp Ser Asn Gly Pro Gln Thr Gly Thr Pro Thr Glu Ser Asn
                 405                 410                 415
Lys Gln Cys Ala Ala Lys Asp Tyr Val Thr Leu Thr Ala Cys Leu Phe
                 420                 425                 430
Val Ala Tyr Met Phe Arg Arg Tyr Asn Ser Val Thr Gly Ser Ser Ser
                 435                 440                 445
```

```
Ser Ile Thr Ala Val Glu Lys Ala Asn
    450                 455
```

<210> SEQ ID NO 2
<211> LENGTH: 468
<212> TYPE: PRT
<213> ORGANISM: Artificial Sequence
<220> FEATURE:
<223> OTHER INFORMATION: SH34GC7

<400> SEQUENCE: 2

```
Ala Thr Pro Ser Ser Ser Pro Glu Leu Pro Leu Lys Pro Ile Pro
1               5                   10                  15

Gly Ser Tyr Gly Trp Pro Leu Leu Gly Pro Ile Leu Asp Arg Leu Asp
            20                  25                  30

Tyr Phe Trp Phe Gln Gly Pro Glu Thr Phe Phe Arg Lys Arg Ile Glu
            35                  40                  45

Lys Tyr Lys Ser Thr Val Phe Arg Ala Asn Val Pro Pro Cys Phe Pro
    50                  55                  60

Phe Phe Ser Asn Val Asn Pro Asn Val Val Val Leu Asp Cys Glu
65                  70                  75                  80

Ser Phe Ala His Leu Phe Asp Met Glu Ile Val Glu Lys Ser Asn Val
                85                  90                  95

Leu Val Gly Asp Phe Met Pro Ser Val Lys Tyr Thr Gly Asn Ile Arg
            100                 105                 110

Val Cys Ala Tyr Leu Asp Thr Ser Glu Pro Gln His Ala Gln Val Lys
            115                 120                 125

Asn Phe Ala Met Asp Ile Leu Lys Arg Ser Ser Lys Val Trp Glu Ser
    130                 135                 140

Glu Val Ile Ser Asn Leu Asp Thr Met Trp Asp Thr Ile Glu Ser Ser
145                 150                 155                 160

Leu Ala Lys Asp Gly Asn Ala Ser Val Ile Phe Pro Leu Gln Lys Phe
                165                 170                 175

Leu Phe Asn Phe Leu Ser Lys Ser Ile Ile Gly Ala Asp Pro Ala Ala
            180                 185                 190

Ser Pro Gln Val Ala Lys Ser Gly Tyr Ala Met Leu Asp Arg Trp Leu
            195                 200                 205

Ala Leu Gln Leu Leu Pro Thr Ile His Ile Gly Val Leu Gln Pro Leu
    210                 215                 220

Val Glu Ile Phe Leu His Ser Trp Ala Tyr Pro Phe Ala Leu Val Ser
225                 230                 235                 240

Gly Asp Tyr Asn Lys Leu Tyr Gln Phe Ile Glu Lys Glu Gly Arg Glu
                245                 250                 255

Ala Val Glu Arg Ala Lys Ala Glu Phe Gly Leu Thr His Gln Glu Ala
            260                 265                 270

Ile His Asn Leu Leu Phe Ile Leu Gly Phe Asn Ala Phe Gly Gly Phe
            275                 280                 285

Ser Ile Phe Leu Pro Thr Leu Leu Ser Asn Ile Leu Ser Asp Thr Thr
    290                 295                 300

Gly Leu Gln Asp Arg Leu Arg Lys Glu Val Arg Ala Lys Gly Gly Pro
305                 310                 315                 320

Ala Leu Ser Phe Ala Ser Val Lys Glu Met Glu Leu Val Lys Ser Val
                325                 330                 335

Val Tyr Glu Thr Leu Arg Leu Asn Pro Pro Val Pro Leu Gln Tyr Ala
            340                 345                 350
```

```
Arg Ala Arg Lys Asp Phe Gln Leu Lys Ser His Asp Ser Val Phe Asp
        355                 360                 365
Ile Lys Lys Gly Glu Leu Leu Cys Gly Tyr Gln Pro Leu Val Met Arg
    370                 375                 380
Asp Ser Lys Val Phe Asp Asp Ala Glu Ser Phe Lys Ala Glu Arg Phe
385                 390                 395                 400
Met Gly Glu Lys Gly Ser Glu Leu Leu Ser Tyr Leu Tyr Trp Ser Asn
                405                 410                 415
Gly Pro Gln Thr Gly Thr Pro Thr Glu Ser Asn Lys Gln Cys Ala Ala
            420                 425                 430
Lys Asp Tyr Val Thr Leu Thr Ala Cys Leu Phe Val Ala Tyr Met Phe
        435                 440                 445
Arg Arg Tyr Asn Ser Val Thr Gly Ser Ser Ser Ile Thr Ala Val
    450                 455                 460
Glu Lys Ala Lys
465

<210> SEQ ID NO 3
<211> LENGTH: 1407
<212> TYPE: DNA
<213> ORGANISM: Artificial Sequence
<220> FEATURE:
<223> OTHER INFORMATION: SH34GC7

<400> SEQUENCE: 3
gctactcctt cttcctcctc ccctgaactc ccgctgaaac cgatcccggg cagctacggg      60
tggcccctcc tcggcccgat attggaccgc ctggactact tctggttcca aggcccggag     120
acgttcttca ggaagaggat cgagaagtac aagagcaccg tgttccgcgc gaacgtgcct     180
ccgtgcttcc ccttcttctc gaacgtgaac cctaacgtcg tggtcgtcct cgattgcgag     240
tccttcgctc acttgttcga catggagatc gtggagaaga gcaacgtcct cgtcggcgac     300
ttcatgccga gcgtgaagta caccgggaac atccgggtct gcgcttacct cgacacttcc     360
gagcctcaac acgctcaggt gaagaacttt gcgatggaca tactgaagag gagctccaaa     420
gtgtgggaga gcgaagtgat ctcgaacttg acaccatgt gggacaccat cgagtccagc     480
ctcgccaagg acggcaacgc cagcgtcatc ttccctctcc aaaagttcct cttcaacttc     540
ctctccaagt ccatcatcgg cgctgacccg gccgcctcgc gcaggtggc caagtccggc     600 tacgccatgc ttgaccggtg gctcgctctc cagctcctcc ccaccatcca cattggcgta     660
ctgcagcctc tagtggagat ttttctgcat tcttgggcat acccttttgc gctggtgagc     720
ggggactaca caagctcta ccagttcatc gagaaggaag ccgagaagc ggtcgaaagg     780 gcgaaggccg agttcggatt gacacaccag gaggccatcc acaacttgct gttcatcctc     840
ggcttcaacg cgttcggcgg cttctcgatc ttcctcccca cgttgctgag caacatactt     900
agcgacacaa ccggactgca ggaccggctg aggaaggagg tccgggcaaa gggagggccg     960
gcgttgagct tcgcctcggt gaaggagatg gaactcgtga agtcggtcgt gtacgagacg    1020
ctgcggctca acccgcccgt cccgctccaa tacgctcgag cccggaagga cttccagctc    1080
aagtcccacg actctgtctt tgatatcaag aaaggcgagc tgctatgcgg gtatcagcct    1140
ttggtcatga gggattcgaa ggtgtttgac gatgctgaga gttttaaggc tgagaggttt    1200
atgggcgaaa agggcagcga gctactgagt tacctgtact ggtccaacgg gccgcagacc    1260
ggaacgccga ccgagtcgaa caagcagtgc gcggctaagg actacgtcac cctcaccgct    1320
```

-continued

```
tgtctcttcg ttgcctacat gtttcgacgg tacaattccg tcacaggaag ctcgagctcg    1380
atcacagccg ttgaaaaggc caagtga                                         1407
```

<210> SEQ ID NO 4
<211> LENGTH: 468
<212> TYPE: PRT
<213> ORGANISM: Artificial Sequence
<220> FEATURE:
<223> OTHER INFORMATION: SH34E8B

<400> SEQUENCE: 4

```
Ala Thr Pro Ser Ser Ser Pro Glu Leu Pro Leu Lys Pro Ile Pro
1               5                   10                  15

Gly Ser Tyr Gly Trp Pro Leu Leu Gly Pro Ile Ser Asp Arg Leu Asp
            20                  25                  30

Tyr Phe Trp Phe Gln Gly Pro Glu Thr Phe Phe Arg Lys Arg Ile Glu
        35                  40                  45

Lys Tyr Lys Ser Thr Val Phe Arg Ala Asn Val Pro Pro Cys Phe Pro
    50                  55                  60

Phe Phe Ser Asn Val Asn Pro Asn Val Val Val Leu Asp Cys Glu
65                  70                  75                  80

Ser Phe Ala His Leu Phe Asp Met Glu Ile Val Glu Lys Ser Asn Val
                85                  90                  95

Leu Val Gly Asp Phe Met Pro Ser Val Lys Tyr Thr Gly Asn Ile Arg
            100                 105                 110

Val Cys Ala Tyr Leu Asp Thr Ser Glu Pro Gln His Ala Gln Val Lys
        115                 120                 125

Asn Phe Ala Met Asp Ile Leu Lys Arg Ser Ser Lys Val Trp Glu Ser
    130                 135                 140

Glu Val Ile Ser Asn Leu Asp Thr Met Trp Asp Thr Ile Glu Ser Ser
145                 150                 155                 160

Leu Ala Lys Asp Gly Asn Ala Ser Val Ile Phe Pro Leu Gln Lys Phe
                165                 170                 175

Leu Phe Asn Phe Leu Ser Lys Ser Ile Ile Gly Ala Asp Pro Ala Ala
            180                 185                 190

Ser Pro Gln Val Ala Lys Ser Gly Tyr Ala Met Leu Asp Arg Trp Leu
        195                 200                 205

Ala Leu Gln Leu Leu Pro Thr Ile His Ile Gly Val Leu Gln Pro Leu
    210                 215                 220

Val Glu Ile Phe Leu His Ser Trp Ala Tyr Pro Phe Ala Leu Val Ser
225                 230                 235                 240

Gly Asp Tyr Asn Lys Leu Tyr Gln Phe Ile Glu Lys Glu Gly Arg Glu
                245                 250                 255

Ala Val Glu Arg Ala Lys Ala Glu Phe Gly Leu Thr His Gln Glu Ala
            260                 265                 270

Ile His Asn Leu Leu Phe Ile Leu Gly Phe Asn Ala Phe Gly Gly Phe
        275                 280                 285

Ser Ile Phe Leu Pro Thr Leu Leu Ser Asn Ile Leu Ser Asp Thr Thr
    290                 295                 300

Gly Leu Gln Asp Arg Leu Arg Lys Glu Val Arg Ala Lys Gly Gly Pro
305                 310                 315                 320

Ala Leu Ser Phe Ala Ser Val Lys Glu Met Glu Leu Val Lys Ser Val
                325                 330                 335

Val Tyr Glu Thr Leu Arg Leu Asn Pro Pro Val Pro Leu Gln Tyr Ala
            340                 345                 350
```

```
Arg Ala Arg Lys Asp Phe Gln Leu Lys Ser His Asp Ser Val Phe Asp
        355                 360                 365

Val Lys Lys Gly Glu Leu Leu Cys Gly Tyr Gln Pro Leu Val Met Arg
    370                 375                 380

Asp Ser Lys Val Phe Asp Asp Ala Glu Ser Phe Lys Ala Glu Arg Phe
385                 390                 395                 400

Met Gly Glu Lys Gly Ser Glu Leu Leu Ser Tyr Leu Tyr Trp Ser Asn
                405                 410                 415

Gly Pro Gln Thr Gly Thr Pro Thr Glu Ser Asn Lys Gln Cys Ala Ala
                420                 425                 430

Lys Asp Tyr Val Thr Leu Thr Ala Cys Leu Phe Val Ala Tyr Met Phe
                435                 440                 445

Arg Arg Tyr Asn Ser Val Thr Gly Ser Ser Ser Ile Thr Ala Val
    450                 455                 460

Glu Lys Ala Lys
465

<210> SEQ ID NO 5
<211> LENGTH: 1407
<212> TYPE: DNA
<213> ORGANISM: Artificial Sequence
<220> FEATURE:
<223> OTHER INFORMATION: SH34E8B

<400> SEQUENCE: 5
gctactcctt cttcctcctc ccctgaactc ccgctgaaac cgatcccggg cagctacggg      60
tggcccctcc tcggcccgat atcggaccgc ctggactact tctggttcca aggcccggag     120
acgttcttca ggaagaggat cgagaagtac aagagcaccg tgttccgcgc gaacgtgcct     180
ccgtgcttcc ccttcttctc gaacgtgaac cctaacgtcg tggtcgtcct cgattgcgag     240
tccttcgctc acttgttcga catggagatc gtggagaaga gcaacgtcct cgtcggcgac     300
ttcatgccga gcgtgaagta caccgggaac atccgggtct gcgcttacct cgacacttcc     360
gagcctcaac acgctcaggt gaagaacttt gcgatggaca tactgaagag gagctccaaa     420
gtgtgggaga gcgaagtgat ctcgaacttg acaccatgt gggacaccat cgagtccagc     480
ctcgccaagg acggcaacgc cagcgtcatc ttccctctcc aaaagttcct cttcaacttc     540
ctctccaagt ccatcatcgg cgctgacccg gccgcctcgc gcaggtggc caagtccggc     600 tacgccatgc ttgaccggtg gctcgctctc cagctcctcc ccaccatcca cattggcgta     660
ctgcagcctc tagtggagat ttttctgcat tcttgggcat accctttgc gctggtgagc     720 ggggactaca caagctcta ccagttcatc gagaaggaag ccgagaagc ggtcgaaagg     780 gcgaaggccg agttcggatt gacacaccag gaggccatcc acaacttgct gttcatcctc     840
ggcttcaacg cgttcggcgg cttctcgatc ttcctcccca cgttgctgag caacatactt     900
agcgacacaa ccggactgca ggaccggctg aggaaggagg tccgggcaaa gggagggccg     960
gcgttgagct tcgcctcggt gaaggagatg gaactcgtga agtcggtcgt gtacgagacg    1020
ctgcggctca acccgcccgt cccgctccaa tacgctcgag cccggaagga cttccagctc    1080
aagtcccacg actctgtctt tgatgtcaag aaaggcgagc tgctatgcgg gtatcagcct    1140
ttggtcatga gggattcgaa ggtgtttgac gatgctgaga gttttaaggc tgagaggttt    1200
atgggcgaaa agggcagcga gctactgagt tacctgtact ggtccaacgg gccgcagacc    1260
ggaacgccga ccgagtcgaa caagcagtgc gcggctaagg actacgtcac cctcaccgct    1320
```

```
tgtctcttcg ttgcctacat gtttcgacgg tacaattccg tcacaggaag ctcgagctcg    1380
atcacagccg ttgaaaaggc caagtga                                        1407
```

<210> SEQ ID NO 6
<211> LENGTH: 468
<212> TYPE: PRT
<213> ORGANISM: Artificial Sequence
<220> FEATURE:
<223> OTHER INFORMATION: SH33AC5

<400> SEQUENCE: 6

```
Ala Thr Pro Ser Ser Ser Pro Glu Leu Pro Leu Lys Pro Ile Pro
1               5                   10                  15

Gly Ser Tyr Gly Trp Pro Leu Leu Gly Pro Ile Leu Asp Arg Leu Asp
            20                  25                  30

Tyr Phe Trp Phe Gln Gly Pro Glu Thr Phe Phe Arg Lys Arg Ile Glu
        35                  40                  45

Lys Tyr Lys Ser Thr Val Phe Arg Ala Asn Val Pro Pro Cys Phe Pro
    50                  55                  60

Phe Phe Ser Asn Val Asn Pro Asn Val Val Val Leu Asp Cys Glu
65                  70                  75                  80

Ser Phe Ala His Leu Phe Asp Met Glu Ile Val Glu Lys Ser Asn Val
                85                  90                  95

Leu Val Gly Asp Phe Met Pro Ser Val Lys Tyr Thr Gly Asn Ile Arg
            100                 105                 110

Val Cys Ala Tyr Leu Asp Thr Ser Glu Pro Gln His Ala Gln Val Lys
        115                 120                 125

Asn Phe Ala Met Asp Ile Leu Lys Arg Ser Ser Lys Val Trp Glu Ser
    130                 135                 140

Glu Val Ile Ser Asn Leu Asp Thr Met Trp Asp Thr Ile Glu Ser Ser
145                 150                 155                 160

Leu Ala Lys Asp Gly Asn Ala Ser Val Ile Phe Pro Leu Gln Lys Phe
                165                 170                 175

Leu Phe Asn Phe Leu Ser Lys Ser Ile Ile Gly Ala Asp Pro Ala Ala
            180                 185                 190

Ser Pro Gln Val Ala Lys Ser Gly Tyr Ala Met Leu Asp Arg Trp Leu
        195                 200                 205

Ala Leu Gln Leu Leu Pro Thr Ile His Ile Gly Val Leu Gln Pro Leu
    210                 215                 220

Val Glu Ile Phe Leu His Ser Trp Ala Tyr Pro Phe Ala Leu Val Ser
225                 230                 235                 240

Gly Asp Tyr Asn Lys Leu Tyr Gln Phe Ile Glu Lys Glu Gly Arg Glu
                245                 250                 255

Ala Val Glu Arg Ala Lys Ala Glu Phe Gly Leu Thr His Gln Glu Ala
            260                 265                 270

Ile His Asn Leu Leu Phe Ile Leu Gly Phe Asn Ala Phe Gly Gly Phe
        275                 280                 285

Ser Ile Phe Leu Pro Thr Leu Leu Ser Asn Ile Leu Ser Asp Thr Thr
    290                 295                 300

Gly Leu Gln Asp Arg Leu Arg Lys Glu Val Arg Ala Lys Gly Gly Pro
305                 310                 315                 320

Ala Leu Ser Phe Ala Ser Val Lys Glu Met Glu Leu Val Lys Ser Val
                325                 330                 335

Val Tyr Glu Thr Leu Arg Leu Asn Pro Pro Val Pro Leu Gln Phe Ala
            340                 345                 350
```

```
Arg Ala Arg Lys Asp Phe Gln Leu Arg Ser His Asp Ser Val Tyr Asp
            355                 360                 365
Ile Lys Lys Gly Glu Leu Leu Cys Gly Tyr Gln Pro Leu Val Met Arg
    370                 375                 380
Asp Ser Lys Val Phe Asp Asp Ala Glu Ser Phe Lys Ala Glu Arg Phe
385                 390                 395                 400
Met Gly Glu Lys Gly Ser Glu Leu Leu Ser Tyr Leu Tyr Trp Ser Asn
                405                 410                 415
Gly Pro Gln Thr Gly Thr Pro Thr Glu Ser Asn Lys Gln Cys Ala Ala
            420                 425                 430
Lys Asp Tyr Val Thr Leu Thr Ala Cys Leu Phe Val Ala Tyr Met Phe
        435                 440                 445
Arg Arg Tyr Asn Ser Val Thr Gly Ser Ser Ser Ile Thr Ala Val
    450                 455                 460
Glu Lys Ala Lys
465

<210> SEQ ID NO 7
<211> LENGTH: 1409
<212> TYPE: DNA
<213> ORGANISM: Artificial Sequence
<220> FEATURE:
<223> OTHER INFORMATION: SH33AC5

<400> SEQUENCE: 7
acgctactcc ttcttcctcc tccoctgaac tcccgctgaa accgatcccg ggcagctacg     60
ggtggcccct cctcggcccg atattggacc gcctggacta cttctggttc caaggcccgg    120
agacgttctt caggaagagg atcgagaagt acaagagcac cgtgttccgc gcgaacgtgc    180
ctccgtgctt ccccttcttc tcgaacgtga accctaacgt cgtggtcgtc ctcgattgcg    240
agtccttcgc tcacttgttc gacatggaga tcgtggagaa gagcaacgtc ctcgtcggcg    300
acttcatgcc gagcgtgaag tacaccggga acatccgggt ctgcgcttac ctcgacactt    360
ccgagcctca acacgctcag gtgaagaact ttgcgatgga catactgaag aggagctcca    420
aagtgtggga gagcgaagtg atctcgaact tggacaccat cgtgggacac catcgagtcca   480 gcctcgccaa ggacggcaac gccagcgtca tcttccctct ccaaaagttc ctcttcaact    540
tcctctccaa gtccatcatc ggcgctgacc cggccgcctc gccgcaggtg gccaagtccg    600
gctacgccat gcttgaccgg tggctcgctc tccagctcct ccccaccatc cacattggcg    660
tactgcagcc tctagtggag attttctctgc attcttgggc ataccctttt gcgctggtga    720
gcggggacta caacaagctc taccagttca tcgagaagga aggccgagaa gcggtcgaaa    780
gggcgaaggc cgagttcgga ttgacacacc aggaggccat ccacaacttg ctgttcatcc    840
tcggcttcaa cgcgttcggc ggcttctcga tcttcctccc cacgttgctg agcaacatac    900
ttagcgacac aaccgactg caggaccggc tgaggaagga ggtccgggca agggagggc     960 cggcgttgag cttcgcctcg gtgaaggaga tggaactcgt gaagtcggtc gtgtacgaga   1020
cgctgcggct caacccgccc gtcccgctcc agtttgctcg agcccggaag gacttccagc   1080
tcaggtcgca cgactcggtg tacgatatca agaaggcga ctgctatgc gggtatcagc     1140 ctttggtcat gagggattcg aaggtgtttg acgatgctga gagttttaag gctgagaggt   1200
ttatgggcga aaagggcagc gagctactga gttacctgta ctggtccaac gggccgcaga   1260
ccggaacgcc gaccgagtcg aacaagcagt gcgcggctaa ggactacgtc accctcaccg   1320
```

```
cttgtctctt cgttgcctac atgtttcgac ggtacaattc cgtcacagga agctcgagct   1380
cgatcacagc cgttgaaaag gccaagtga                                     1409
```

<210> SEQ ID NO 8
<211> LENGTH: 468
<212> TYPE: PRT
<213> ORGANISM: Artificial Sequence
<220> FEATURE:
<223> OTHER INFORMATION: SH33C2A

<400> SEQUENCE: 8

```
Ala Thr Pro Ser Ser Ser Pro Glu Leu Pro Leu Lys Pro Ile Pro
1               5                   10                  15

Gly Ser Tyr Gly Trp Pro Leu Leu Gly Pro Ile Ser Asp Arg Leu Asp
            20                  25                  30

Tyr Phe Trp Phe Gln Gly Pro Glu Thr Phe Phe Arg Lys Arg Ile Glu
        35                  40                  45

Lys Tyr Lys Ser Thr Val Phe Arg Ala Asn Val Pro Pro Cys Phe Pro
    50                  55                  60

Phe Phe Ser Asn Val Asn Pro Asn Val Val Val Leu Asp Cys Glu
65                  70                  75                  80

Ser Phe Ala His Leu Phe Asp Met Glu Ile Val Glu Lys Ser Asn Val
                85                  90                  95

Leu Val Gly Asp Phe Met Pro Ser Val Lys Tyr Thr Gly Asn Ile Arg
            100                 105                 110

Val Cys Ala Tyr Leu Asp Thr Ser Glu Pro Gln His Ala Gln Val Lys
        115                 120                 125

Asn Phe Ala Met Asp Ile Leu Lys Arg Ser Ser Lys Val Trp Glu Ser
    130                 135                 140

Glu Val Ile Ser Asn Leu Asp Thr Met Trp Asp Thr Ile Glu Ser Ser
145                 150                 155                 160

Leu Ala Lys Asp Gly Asn Ala Ser Val Ile Phe Pro Leu Gln Lys Phe
                165                 170                 175

Leu Phe Asn Phe Leu Ser Lys Ser Ile Ile Gly Ala Asp Pro Ala Ala
            180                 185                 190

Ser Pro Gln Val Ala Lys Ser Gly Tyr Ala Met Leu Asp Arg Trp Leu
        195                 200                 205

Ala Leu Gln Leu Leu Pro Thr Ile His Ile Gly Val Leu Gln Pro Leu
    210                 215                 220

Val Glu Ile Phe Leu His Ser Trp Ala Tyr Pro Phe Ala Leu Val Ser
225                 230                 235                 240

Gly Asp Tyr Asn Lys Leu Tyr Gln Phe Ile Glu Lys Glu Gly Arg Glu
                245                 250                 255

Ala Val Glu Arg Ala Lys Ala Glu Phe Gly Leu Thr His Gln Glu Ala
            260                 265                 270

Ile His Asn Leu Leu Phe Ile Leu Gly Phe Asn Ala Phe Gly Gly Phe
        275                 280                 285

Ser Ile Phe Leu Pro Thr Leu Leu Ser Asn Ile Leu Ser Asp Thr Thr
    290                 295                 300

Gly Leu Gln Asp Arg Leu Arg Lys Glu Val Arg Ala Lys Gly Gly Pro
305                 310                 315                 320

Ala Leu Ser Phe Ala Ser Val Lys Glu Met Glu Leu Val Lys Ser Val
                325                 330                 335

Val Tyr Glu Thr Leu Arg Leu Asn Pro Pro Val Pro Leu Gln Phe Ala
            340                 345                 350
```

Arg Ala Arg Lys Asp Phe Gln Leu Lys Ser His Asp Ser Val Tyr Glu
        355                 360                 365

Ile Lys Lys Gly Glu Leu Leu Cys Gly Tyr Gln Pro Leu Val Met Arg
    370                 375                 380

Asp Ser Lys Val Phe Asp Asp Ala Glu Ser Phe Lys Ala Glu Arg Phe
385                 390                 395                 400

Met Gly Glu Lys Gly Ser Glu Leu Leu Ser Tyr Leu Tyr Trp Ser Asn
                405                 410                 415

Gly Pro Gln Thr Gly Thr Pro Thr Glu Ser Asn Lys Gln Cys Ala Ala
            420                 425                 430

Lys Asp Tyr Val Thr Leu Thr Ala Cys Leu Phe Val Ala Tyr Met Phe
        435                 440                 445

Arg Arg Tyr Asn Ser Val Thr Gly Ser Ser Ser Ile Thr Ala Val
    450                 455                 460

Glu Lys Ala Asn
465

<210> SEQ ID NO 9
<211> LENGTH: 1407
<212> TYPE: DNA
<213> ORGANISM: Artificial Sequence
<220> FEATURE:
<223> OTHER INFORMATION: SH33C2A

<400> SEQUENCE: 9
gctactcctt cttcctcctc ccctgaactc ccgctgaaac cgatcccggg cagctacggg      60
tggcccctcc tcggcccgat atcggaccgc ctggactact tctggttcca aggcccggag     120
acgttcttca ggaagaggat cgagaagtac aagagcaccg tgttccgcgc gaacgtgcct     180
ccgtgcttcc ccttcttctc gaacgtgaac cctaacgtcg tggtcgtcct cgattgcgag     240
tccttcgctc acttgttcga catggagatc gtggagaaga gcaacgtcct cgtcggcgac     300
ttcatgccga gcgtgaagta caccgggaac atccgggtct gcgcttacct cgacacttcc     360
gagcctcaac acgctcaggt gaagaacttt gcgatggaca tactgaagag gagctccaaa     420
gtgtgggaga gcgaagtgat ctcgaacttg gacaccatgt gggacaccat cgagtccagc     480
ctcgccaagg acggcaacgc cagcgtcatc ttccctctcc aaaagttcct cttcaacttc     540
ctctccaagt ccatcatcgg cgctgacccg gccgcctcgc cgcaggtggc caagtccggc     600
tacgccatgc ttgaccggtg gctcgctctc cagctcctcc ccaccatcca cattggcgta     660
ctgcagcctc tagtggagat ttttctgcat tcttgggcat accctttttgc gctggtgagc     720 ggggactaca caagctcta ccagttcatc gagaaggaag gccgagaagc ggtcgaaagg     780
gcgaaggccg agttcggatt gacacaccag gaggccatcc acaacttgct gttcatcctc     840
ggcttcaacg cgttcggcgg cttctcgatc ttcctcccca cgttgctgag caacatactt     900
agcgacacaa ccggactgca ggaccggctg aggaaggagg tccgggcaaa gggagggccg     960
gcgttgagct cgcctcggt gaaggagatg gaactcgtga agtcggtcgt gtacgagacg    1020
ctgcggctca acccgcccgt cccgctccag tttgctcgag cccggaagga cttccagctc    1080
aagtcccacg actctgtcta tgaaatcaag aaaggcgagc tgctatgcgg gtatcagcca    1140
ttggtgatga gggattcgaa ggtgtttgac gatgctgaga gttttaaggc tgagaggttt    1200
atgggcgaaa aggcagcga gctactgagt tacctgtact ggtccaacgg gccgcagacc    1260
ggaacgccga ccgagtcgaa caagcagtgc gcggctaagg actacgtcac cctcaccgct    1320

```
tgtctcttcg ttgcctacat gtttcgacgg tacaattccg tcacaggaag ctcgagctcg    1380
atcacagccg ttgaaaaggc caactga                                        1407
```

<210> SEQ ID NO 10
<211> LENGTH: 468
<212> TYPE: PRT
<213> ORGANISM: Artificial Sequence
<220> FEATURE:
<223> OTHER INFORMATION: SH33B7A

<400> SEQUENCE: 10

```
Ala Thr Pro Ser Ser Ser Pro Glu Leu Pro Leu Lys Pro Ile Pro
1               5                   10                  15

Gly Ser Tyr Gly Trp Pro Leu Leu Gly Pro Ile Leu Asp Arg Leu Asp
                20                  25                  30

Tyr Phe Trp Phe Gln Gly Pro Glu Thr Phe Phe Arg Lys Arg Ile Glu
            35                  40                  45

Lys Tyr Lys Ser Thr Val Phe Arg Ala Asn Val Pro Pro Cys Phe Pro
        50                  55                  60

Phe Phe Ser Asn Val Asn Pro Asn Val Val Val Leu Asp Cys Glu
65                  70                  75                  80

Ser Phe Ala His Leu Phe Asp Met Glu Ile Val Glu Lys Ser Asn Val
                85                  90                  95

Leu Val Gly Asp Phe Met Pro Ser Val Lys Tyr Thr Gly Asn Ile Arg
            100                 105                 110

Val Cys Ala Tyr Leu Asp Thr Ser Glu Pro Gln His Ala Gln Val Lys
        115                 120                 125

Asn Phe Ala Met Asp Ile Leu Lys Arg Ser Ser Lys Val Trp Glu Ser
130                 135                 140

Glu Val Ile Ser Asn Leu Asp Thr Met Trp Asp Thr Ile Glu Ser Ser
145                 150                 155                 160

Leu Ala Lys Asp Gly Asn Ala Ser Val Ile Phe Pro Leu Gln Lys Phe
                165                 170                 175

Leu Phe Asn Phe Leu Ser Lys Ser Ile Ile Gly Ala Asp Pro Ala Ala
            180                 185                 190

Ser Pro Gln Val Ala Lys Ser Gly Tyr Ala Met Leu Asp Arg Trp Leu
        195                 200                 205

Ala Leu Gln Leu Leu Pro Thr Ile His Ile Gly Val Leu Gln Pro Leu
210                 215                 220

Val Glu Ile Phe Leu His Ser Trp Ala Tyr Pro Phe Ala Leu Val Ser
225                 230                 235                 240

Gly Asp Tyr Asn Lys Leu Tyr Gln Phe Ile Glu Lys Glu Gly Arg Glu
                245                 250                 255

Ala Val Glu Arg Ala Lys Ala Glu Phe Gly Leu Thr His Gln Glu Ala
            260                 265                 270

Ile His Asn Leu Leu Phe Ile Leu Gly Phe Asn Ala Phe Gly Gly Phe
        275                 280                 285

Ser Ile Phe Leu Pro Thr Leu Leu Ser Asn Ile Leu Ser Asp Thr Thr
290                 295                 300

Gly Leu Gln Asp Arg Leu Arg Lys Glu Val Arg Ala Lys Gly Gly Pro
305                 310                 315                 320

Ala Leu Ser Phe Ala Ser Val Lys Glu Met Glu Leu Val Lys Ser Val
                325                 330                 335

Val Tyr Glu Thr Leu Arg Leu Asn Pro Pro Val Pro Phe Gln Tyr Ala
            340                 345                 350
```

```
Arg Ala Arg Lys Asp Phe Gln Leu Lys Ser His Asp Ser Val Tyr Asp
            355                 360                 365
Ile Lys Lys Gly Glu Leu Leu Cys Gly Tyr Gln Pro Leu Val Met Arg
    370                 375                 380
Asp Ser Lys Val Phe Asp Asp Ala Glu Ser Phe Lys Ala Glu Arg Phe
385                 390                 395                 400
Met Gly Glu Lys Gly Ser Glu Leu Leu Ser Tyr Leu Tyr Trp Ser Asn
                405                 410                 415
Gly Pro Gln Thr Gly Thr Pro Thr Glu Ser Asn Lys Gln Cys Ala Ala
            420                 425                 430
Lys Asp Tyr Val Thr Leu Thr Ala Cys Leu Phe Val Ala Tyr Met Phe
        435                 440                 445
Arg Arg Tyr Asn Ser Val Thr Gly Ser Ser Ser Ile Thr Ala Val
    450                 455                 460
Glu Lys Ala Lys
465

<210> SEQ ID NO 11
<211> LENGTH: 1407
<212> TYPE: DNA
<213> ORGANISM: Artificial Sequence
<220> FEATURE:
<223> OTHER INFORMATION: SH33B7A

<400> SEQUENCE: 11
gctactcctt cttcctcctc ccctgaactc ccgctgaaac cgatcccggg cagctacggg      60
tggcccctcc tcggcccgat attggaccgc ctggactact tctggttcca aggcccggag     120
acgttcttca ggaagaggat cgagaagtac aagagcaccg tgttccgcgc gaacgtgcct     180
ccgtgcttcc ccttcttctc gaacgtgaac cctaacgtcg tggtcgtcct cgattgcgag     240
tccttcgctc acttgttcga catggagatc gtggagaaga gcaacgtcct cgtcggcgac     300
ttcatgccga gcgtgaagta caccgggaac atccgggtct gcgcttacct cgacacttcc     360
gagcctcaac acgctcaggt gaagaacttt gcgatggaca tactgaagag gagctccaaa     420
gtgtgggaga gcgaagtgat ctcgaacttg acaccatgt gggacaccat cgagtccagc     480
ctcgccaagg acggcaacgc cagcgtcatc ttccctctcc aaaagttcct cttcaacttc     540
ctctccaagt ccatcatcgg cgctgacccg ccgcctcgc cgcaggtggc caagtccggc     600
tacgccatgc ttgaccggtg gctcgctctc cagctcctcc ccaccatcca cattggcgta     660
ctgcagcctc tagtggagat ttttctgcat tcttgggcat acccttttgc gctggtgagc     720
ggggactaca caagctcta ccagttcatc gagaaggaag ccgagaagc ggtcgaaagg      780
gcgaaggccg agttcggatt gacacaccag gaggccatcc acaacttgct gttcatcctc     840
ggcttcaacg cgttcggcgg cttctcgatc ttcctcccca cgttgctgag caacatactt     900
agcgacacaa ccggactgca ggaccggctg aggaaggagg tccgggcaaa gggagggccg     960
gcgttgagct tcgcctcggt gaaggagatg gaactcgtga agtcggtcgt gtacgagacg    1020
ctgcggctca acccgcccgt cccgttccaa tacgctcgag cccggaagga cttccagctc    1080
aagtccacg actcggtgta cgatatcaag aaaggcgagc tgctatgcgg gtatcagcct    1140
ttggtcatga gggattcgaa ggtgtttgac gatgctgaga gttttaaggc tgagaggttt    1200
atgggcgaaa aggcagcga gctactgagt tacctgtact ggtccaacgg gccgcagacc    1260
ggaacgccga ccgagtcgaa caagcagtgc gcggctaagg actacgtcac cctcaccgct    1320
```

```
tgtctcttcg ttgcctacat gtttcgacgg tacaattccg tcacaggaag ctcgagctcg    1380
atcacagccg ttgaaaaggc caagtga                                        1407
```

<210> SEQ ID NO 12
<211> LENGTH: 466
<212> TYPE: PRT
<213> ORGANISM: Artificial Sequence
<220> FEATURE:
<223> OTHER INFORMATION: SH30D10A

<400> SEQUENCE: 12

```
Ala Thr Pro Ser Ser Ser Pro Glu Leu Pro Leu Lys Pro Ile Pro
1               5                   10                  15

Gly Ser Tyr Gly Trp Pro Leu Leu Gly Pro Ile Ser Asp Arg Leu Asp
                20                  25                  30

Tyr Phe Trp Phe Gln Gly Pro Glu Thr Phe Phe Arg Lys Arg Ile Glu
            35                  40                  45

Lys Tyr Lys Ser Thr Val Phe Arg Ala Asn Val Pro Pro Cys Phe Pro
        50                  55                  60

Phe Phe Ser Asn Val Asn Pro Asn Val Val Val Leu Asp Cys Glu
65                  70                  75                  80

Ser Phe Ala His Leu Phe Asp Met Glu Ile Val Glu Lys Ser Asn Val
                85                  90                  95

Leu Val Gly Asp Phe Met Pro Ser Val Lys Tyr Thr Gly Asn Ile Arg
            100                 105                 110

Val Cys Ala Tyr Leu Asp Thr Ser Glu Pro Gln His Ala Gln Val Lys
        115                 120                 125

Asn Phe Ala Met Asp Ile Leu Lys Arg Ser Ser Lys Val Trp Glu Ser
130                 135                 140

Glu Val Ile Ser Asn Leu Asp Thr Met Trp Asp Thr Ile Glu Ser Ser
145                 150                 155                 160

Leu Ala Lys Asp Gly Asn Ala Ser Val Ile Phe Pro Leu Gln Lys Phe
                165                 170                 175

Leu Phe Asn Phe Leu Ser Lys Ser Ile Ile Gly Ala Asp Pro Ala Ala
            180                 185                 190

Ser Pro Gln Val Ala Lys Ser Gly Tyr Ala Met Leu Asp Arg Trp Leu
        195                 200                 205

Ala Leu Gln Leu Leu Pro Thr Ile His Ile Gly Val Leu Gln Pro Leu
210                 215                 220

Val Glu Ile Phe Leu His Ser Trp Ala Tyr Pro Phe Ala Leu Val Ser
225                 230                 235                 240

Gly Asp Tyr Asn Lys Leu Tyr Gln Phe Ile Glu Lys Glu Gly Arg Glu
                245                 250                 255

Ala Val Glu Arg Ala Lys Ala Glu Phe Gly Leu Thr His Gln Glu Ala
            260                 265                 270

Ile His Asn Leu Leu Phe Ile Leu Gly Phe Asn Ala Phe Gly Gly Phe
        275                 280                 285

Ser Ile Phe Leu Pro Thr Leu Leu Ser Asn Ile Leu Ser Asp Thr Thr
290                 295                 300

Gly Leu Gln Asp Arg Leu Arg Lys Glu Val Arg Ala Lys Gly Gly Pro
305                 310                 315                 320

Ala Leu Ser Phe Ala Ser Val Lys Glu Met Glu Leu Val Lys Ser Val
                325                 330                 335

Val Tyr Glu Thr Leu Arg Leu Asn Pro Pro Val Pro Phe Gln Tyr Ala
            340                 345                 350
```

```
Arg Ala Arg Lys Asp Phe Gln Leu Lys Ser His Asp Ser Val Phe Asp
        355                 360                 365
Ile Lys Lys Gly Glu Leu Leu Cys Gly Tyr Gln Lys Val Val Met Thr
    370                 375                 380
Asp Pro Lys Val Phe Asp Glu Pro Glu Ser Asn Ser Asp Arg Phe
385                 390                 395                 400
Val Gln Asn Ser Glu Leu Leu Asn Tyr Leu Tyr Trp Ser Asn Gly Pro
                405                 410                 415
Gln Thr Gly Thr Pro Thr Glu Ser Asn Lys Gln Cys Ala Ala Lys Asp
                420                 425                 430
Tyr Val Thr Leu Thr Ala Cys Leu Phe Val Ala Tyr Met Phe Arg Arg
                435                 440                 445
Tyr Asn Ser Val Thr Gly Ser Ser Ser Ser Ile Thr Ala Val Glu Lys
                450                 455                 460
Ala Asn
465

<210> SEQ ID NO 13
<211> LENGTH: 1401
<212> TYPE: DNA
<213> ORGANISM: Artificial Sequence
<220> FEATURE:
<223> OTHER INFORMATION: SH30D10A

<400> SEQUENCE: 13
gctactcctt cttcctcctc ccctgaactc ccgctgaaac cgatcccggg cagctacggg      60
tggcccctcc tcggcccgat atcggaccgc ctggactact tctggttcca aggcccggag     120
acgttcttca ggaagaggat cgagaagtac aagagcaccg tgttccgcgc gaacgtgcct     180
ccgtgcttcc ccttcttctc gaacgtgaac cctaacgtcg tggtcgtcct cgattgcgag     240
tccttcgctc acttgttcga catggagatc gtggagaaga gcaacgtcct cgtcggcgac     300
ttcatgccga gcgtgaagta caccgggaac atccgggtct gcgcttacct cgacacttcc     360
gagcctcaac acgctcaggt gaagaacttt gcgatggaca tactgaagag gagctccaaa     420
gtgtgggaga gcgaagtgat ctcgaacttg acaccatgt gggacaccat cgagtccagc     480
ctcgccaagg acggcaacgc cagcgtcatc ttccctctcc aaaagttcct cttcaacttc     540
ctctccaagt ccatcatcgg cgctgacccg gccgcctcgc gcaggtggc caagtccggc     600
tacgccatgc ttgaccggtg gctcgctctc cagctcctcc ccaccatcca cattggcgta     660
ctgcagcctc tagtggagat ttttctgcat tcttgggcat acccttttgc gctggtgagc     720
ggggactaca caagctcta ccagttcatc gagaaggaag ccgagaagc ggtcgaaagg     780
gcgaaggccg agttcggatt gacacaccag gaggccatcc acaacttgct gttcatcctc     840
ggcttcaacg cgttcggcgg cttctcgatc ttcctcccca cgttgctgag caacatactt     900
agcgacacaa ccggactgca ggaccggctg aggaaggagg tccgggcaaa gggagggccg     960
gcgttgagct tcgcctcggt gaaggagatg gaactcgtga agtcggtcgt gtacgagacg    1020
ctgcggctca acccgcccgt cccgttccaa tacgctcgag cccggaagga cttccagctc    1080
aagtccacg actctgtctt tgatatcaag aaggcgagc tgctatgcgg gtatcagaag    1140
gtggtgatga cagacccgaa agtgttcgac gaaccggaga gcttcaactc ggaccggttc    1200
gtccaaaaca gcgagctact gaattacctg tactggtcca acgggccgca gaccggaacg    1260
ccgaccgagt cgaacaagca gtgcgcggct aaggactacg tcaccctcac cgcttgtctc    1320
```

-continued

```
ttcgttgcct acatgtttcg acggtacaat tccgtcacag gaagctcgag ctcgatcaca    1380
gccgttgaaa aggccaactg a                                               1401
```

<210> SEQ ID NO 14
<211> LENGTH: 468
<212> TYPE: PRT
<213> ORGANISM: Artificial Sequence
<220> FEATURE:
<223> OTHER INFORMATION: SH324E10

<400> SEQUENCE: 14

```
Ala Thr Pro Ser Ser Ser Pro Glu Leu Pro Leu Lys Pro Ile Pro
1               5                  10                  15

Gly Ser Tyr Gly Trp Pro Leu Leu Gly Pro Ile Ser Asp Arg Leu Asp
            20                  25                  30

Tyr Phe Trp Phe Gln Gly Pro Glu Thr Phe Phe Arg Lys Arg Ile Glu
        35                  40                  45

Lys Tyr Lys Ser Thr Val Phe Arg Ala Asn Val Pro Pro Cys Phe Pro
    50                  55                  60

Phe Phe Ser Asn Val Asn Pro Asn Val Val Val Leu Asp Cys Glu
65                  70                  75                  80

Ser Phe Ala His Leu Phe Asp Met Glu Ile Val Glu Lys Ser Asn Val
                85                  90                  95

Leu Val Gly Asp Phe Met Pro Ser Val Lys Tyr Thr Gly Asn Ile Arg
            100                 105                 110

Val Cys Ala Tyr Leu Asp Thr Ser Glu Pro Gln His Ala Gln Val Lys
        115                 120                 125

Asn Phe Ala Met Asp Ile Leu Lys Arg Ser Ser Lys Val Trp Glu Ser
    130                 135                 140

Glu Val Ile Ser Asn Leu Asp Thr Met Trp Asp Thr Ile Glu Ser Ser
145                 150                 155                 160

Leu Ala Lys Asp Gly Asn Ala Ser Val Ile Phe Pro Leu Gln Lys Phe
                165                 170                 175

Leu Phe Asn Phe Leu Ser Lys Ser Ile Ile Gly Ala Asp Pro Ala Ala
            180                 185                 190

Ser Pro Gln Val Ala Lys Ser Gly Tyr Ala Met Leu Asp Arg Trp Leu
        195                 200                 205

Ala Leu Gln Leu Leu Pro Thr Ile His Ile Gly Val Leu Gln Pro Leu
    210                 215                 220

Val Glu Ile Phe Leu His Ser Trp Ala Tyr Pro Phe Ala Leu Val Ser
225                 230                 235                 240

Gly Asp Tyr Asn Lys Leu Tyr Gln Phe Ile Glu Lys Glu Gly Arg Glu
                245                 250                 255

Ala Val Glu Arg Ala Lys Ala Glu Phe Gly Leu Thr His Gln Glu Ala
            260                 265                 270

Ile His Asn Leu Leu Phe Ile Leu Gly Phe Asn Ala Phe Gly Gly Phe
        275                 280                 285

Ser Ile Phe Leu Pro Thr Leu Leu Ser Asn Ile Leu Ser Asp Thr Thr
    290                 295                 300

Gly Leu Gln Asp Arg Leu Arg Lys Glu Val Arg Ala Lys Gly Gly Pro
305                 310                 315                 320

Ala Leu Ser Phe Ala Ser Val Lys Glu Met Glu Leu Val Lys Ser Val
                325                 330                 335

Val Tyr Glu Thr Leu Arg Leu Asn Pro Pro Val Pro Phe Gln Tyr Ala
            340                 345                 350
```

```
Arg Ala Arg Lys Asp Phe Gln Leu Lys Ser His Asp Ser Val Phe Asp
            355                 360                 365
Ile Lys Lys Gly Glu Leu Leu Cys Gly Tyr Gln Pro Leu Val Met Arg
        370                 375                 380
Asp Ser Lys Val Phe Asp Asp Ala Glu Ser Phe Lys Ala Glu Arg Phe
385                 390                 395                 400
Met Gly Glu Lys Gly Ser Glu Leu Leu Ser Tyr Leu Tyr Trp Ser Asn
                405                 410                 415
Gly Pro Gln Thr Gly Thr Pro Thr Glu Ser Asn Lys Gln Cys Ala Ala
            420                 425                 430
Lys Asp Tyr Val Thr Leu Thr Ala Cys Leu Phe Val Ala Tyr Met Phe
        435                 440                 445
Arg Arg Tyr Asn Ser Val Thr Gly Ser Ser Ser Ile Thr Ala Val
    450                 455                 460
Glu Lys Ala Asn
465

<210> SEQ ID NO 15
<211> LENGTH: 1407
<212> TYPE: DNA
<213> ORGANISM: Artificial Sequence
<220> FEATURE:
<223> OTHER INFORMATION: SH324E10

<400> SEQUENCE: 15
gctactcctt cttcctcctc ccctgaactc ccgctgaaac cgatcccggg cagctacggg      60
tggcccctcc tcggcccgat atcggaccgc ctggactact tctggttcca aggcccggag     120
acgttcttca ggaagaggat cgagaagtac aagagcaccg tgttccgcgc gaacgtgcct     180
ccgtgcttcc ccttcttctc gaacgtgaac cctaacgtcg tggtcgtcct cgattgcgag     240
tccttcgctc acttgttcga catggagatc gtggagaaga gcaacgtcct cgtcggcgac     300
ttcatgccga gcgtgaagta caccgggaac atccgggtct gcgcttacct cgacacttcc     360
gagcctcaac acgctcaggt gaagaacttt gcgatggaca tactgaagag gagctccaaa     420
gtgtgggaga gcgaagtgat ctcgaacttg acaccatgt gggacaccat cgagtccagc     480
ctcgccaagg acggcaacgc cagcgtcatc ttccctctcc aaaagttcct cttcaacttc     540
ctctccaagt ccatcatcgg cgctgacccg gccgcctcgc cgcaggtggc caagtccggc     600
tacgccatgc ttgaccggtg gctcgctctc cagctcctcc ccaccatcca cattggcgta     660
ctgcagcctc tagtggagat ttttctgcat tcttgggcat acccttttgc gctggtgagc     720
ggggactaca acaagctcta ccagttcatc gagaaggaag ccgagaagc ggtcgaaagg     780 gcgaaggccg agttcggatt gacacaccag gaggccatcc acaacttgct gttcatcctc     840
ggcttcaacg cgttcggcgg cttctcgatc ttcctcccca cgttgctgag caacatactt     900
agcgacacaa ccggactgca ggaccggctg aggaaggagg tccgggcaaa gggagggccg     960
gcgttgagct tcgcctcggt gaaggagatg gaactcgtga agtcggtcgt gtacgagacg    1020
ctgcggctca acccgcccgt cccgttccaa tacgctcgag cccggaagga cttccagctc    1080
aagtcccacg actctgtctt tgatatcaag aaaggcgagc tgctatgcgg gtatcagcct    1140
ttggtcatga gggattcgaa ggtgtttgac gatgctgaga gttttaaggc tgagaggttt    1200
atgggcgaaa aggcagcga gctactgagt tacctgtact ggtccaacgg gccgcagacc    1260
ggaacgccga ccgagtcgaa caagcagtgc gcggctaagg actacgtcac cctcaccgct    1320
```

```
tgtctcttcg ttgcctacat gtttcgacgg tacaattccg tcacaggaag ctcgagctcg    1380
atcacagccg ttgaaaaggc caactga                                        1407
```

<210> SEQ ID NO 16
<211> LENGTH: 468
<212> TYPE: PRT
<213> ORGANISM: Artificial Sequence
<220> FEATURE:
<223> OTHER INFORMATION: SH329D3

<400> SEQUENCE: 16

```
Ala Thr Pro Ser Ser Ser Pro Glu Leu Pro Leu Lys Pro Ile Pro
1               5                   10                  15

Gly Ser Tyr Gly Trp Pro Leu Leu Gly Pro Ile Leu Asp Arg Leu Asp
            20                  25                  30

Tyr Phe Trp Phe Gln Gly Pro Glu Thr Phe Phe Arg Lys Arg Ile Glu
        35                  40                  45

Lys Tyr Lys Ser Thr Val Phe Arg Ala Asn Val Pro Pro Cys Phe Pro
    50                  55                  60

Phe Phe Ser Asn Val Asn Pro Asn Val Val Val Leu Asp Cys Glu
65                  70                  75                  80

Ser Phe Ala His Leu Phe Asp Met Glu Ile Val Glu Lys Ser Asn Val
                85                  90                  95

Leu Val Gly Asp Phe Met Pro Ser Val Lys Tyr Thr Gly Asn Ile Arg
            100                 105                 110

Val Cys Ala Tyr Leu Asp Thr Ser Glu Pro Gln His Ala Gln Val Lys
        115                 120                 125

Asn Phe Ala Met Asp Ile Leu Lys Arg Ser Ser Lys Val Trp Glu Ser
    130                 135                 140

Glu Val Ile Ser Asn Leu Asp Thr Met Trp Asp Thr Ile Glu Ser Ser
145                 150                 155                 160

Leu Ala Lys Asp Gly Asn Ala Ser Val Ile Phe Pro Leu Gln Lys Phe
                165                 170                 175

Leu Phe Asn Phe Leu Ser Lys Ser Ile Ile Gly Ala Asp Pro Ala Ala
            180                 185                 190

Ser Pro Gln Val Ala Lys Ser Gly Tyr Ala Met Leu Asp Arg Trp Leu
        195                 200                 205

Ala Leu Gln Leu Leu Pro Thr Ile His Ile Gly Val Leu Gln Pro Leu
    210                 215                 220

Val Glu Ile Phe Leu His Ser Trp Ala Tyr Pro Phe Ala Leu Val Ser
225                 230                 235                 240

Gly Asp Tyr Asn Lys Leu Tyr Gln Phe Ile Glu Lys Glu Gly Arg Glu
                245                 250                 255

Ala Val Glu Arg Ala Lys Ala Glu Phe Gly Leu Thr His Gln Glu Ala
            260                 265                 270

Ile His Asn Leu Leu Phe Ile Leu Gly Phe Asn Ala Phe Gly Gly Phe
        275                 280                 285

Ser Ile Phe Leu Pro Thr Leu Leu Ser Asn Ile Leu Ser Asp Thr Thr
    290                 295                 300

Gly Leu Gln Asp Arg Leu Arg Lys Glu Val Arg Ala Lys Gly Gly Pro
305                 310                 315                 320

Ala Leu Ser Phe Ala Ser Val Lys Glu Met Glu Leu Val Lys Ser Val
                325                 330                 335

Val Tyr Glu Thr Leu Arg Leu Asn Pro Pro Val Pro Leu Gln Phe Ala
            340                 345                 350
```

```
Arg Ala Arg Lys Asp Phe Gln Leu Ser Ser Tyr Asp Ser Val Tyr Asp
        355                 360                 365

Ile Lys Lys Gly Glu Leu Leu Cys Gly Tyr Gln Pro Leu Val Met Arg
    370                 375                 380

Asp Ser Lys Val Phe Asp Asp Ala Glu Ser Phe Lys Ala Glu Arg Phe
385                 390                 395                 400

Met Gly Glu Lys Gly Ser Glu Leu Leu Ser Tyr Leu Tyr Trp Ser Asn
                405                 410                 415

Gly Pro Gln Thr Gly Thr Pro Thr Glu Ser Asn Lys Gln Cys Ala Ala
            420                 425                 430

Lys Asp Tyr Val Thr Leu Thr Ala Cys Leu Phe Val Ala Tyr Met Phe
        435                 440                 445

Arg Arg Tyr Asn Ser Val Thr Gly Ser Ser Ser Ile Thr Ala Val
    450                 455                 460

Glu Lys Ala Lys
465

<210> SEQ ID NO 17
<211> LENGTH: 1407
<212> TYPE: DNA
<213> ORGANISM: Artificial Sequence
<220> FEATURE:
<223> OTHER INFORMATION: SH329D3

<400> SEQUENCE: 17
gctactcctt cttcctcctc ccctgaactc ccgctgaaac cgatcccggg cagctacggg      60
tggcccctcc tcggcccgat attggaccgc ctggactact tctggttcca aggcccggag     120
acgttcttca ggaagaggat cgagaagtac aagagcaccg tgttccgcgc gaacgtgcct     180
ccgtgcttcc ccttcttctc gaacgtgaac cctaacgtcg tggtcgtcct cgattgcgag     240
tccttcgctc acttgttcga catggagatc gtggagaaga gcaacgtcct cgtcggcgac     300
ttcatgccga gcgtgaagta caccgggaac atccgggtct gcgcttacct cgacacttcc     360
gagcctcaac acgctcaggt gaagaacttt gcgatggaca tactgaagag gagctccaaa     420
gtgtgggaga gcgaagtgat ctcgaacttg gacaccatgt gggacaccat cgagtccagc     480
ctcgccaagg acggcaacgc cagcgtcatc ttccctctcc aaaagttcct cttcaacttc     540
ctctccaagt ccatcatcgg cgctgacccg gccgcctcgc cgcaggtggc caagtccggc     600
tacgccatgc ttgaccggtg gctcgctctc cagctcctcc ccaccatcca cattggcgta     660
ctgcagcctc tagtggagat ttttctgcat tcttgggcat accctttgc gctggtgagc     720 ggggactaca caagctcta ccagttcatc gagaaggaag gccgagaagc ggtcgaaagg     780
gcgaaggccg agttcggatt gacacaccag gaggccatcc acaacttgct gttcatcctc     840
ggcttcaacg cgttcggcgg cttctcgatc ttcctcccca cgttgctgag caacatactt     900
agcgacacaa ccggactgca ggaccggctg aggaaggagg tccgggcaaa gggagggccg     960
gcgttgagct tcgcctcggt gaaggagatg gaactcgtga agtcggtcgt gtacgagacg    1020
ctgcggctca acccgcccgt cccgctccag tttgctcgag cccggaagga cttccagctc    1080
agctcgtacg actcggtgta cgatatcaag aaaggcgagc tgctatgcgg gtatcagcct    1140
ttggtcatga gggattcgaa ggtgtttgac gatgctgaga gttttaaggc tgagaggttt    1200
atgggcgaaa agggcagcga gctactgagt tacctgtact ggtccaacgg gccgcagacc    1260
ggaacgccga ccgagtcgaa caagcagtgc gcggctaagg actacgtcac cctcaccgct    1320
```

```
tgtctcttcg ttgcctacat gtttcgacgg tacaattccg tcacaggaag ctcgagctcg    1380
atcacagccg ttgaaaaggc caagtga                                        1407

<210> SEQ ID NO 18
<211> LENGTH: 9
<212> TYPE: PRT
<213> ORGANISM: Cucumis melo
<220> FEATURE:
<223> OTHER INFORMATION: 9-hydroperoxide lyase from Cucumis melo

<400> SEQUENCE: 18

Ala Thr Pro Ser Ser Ser Ser Pro Glu
1               5
```